United States Patent
Liu et al.

(10) Patent No.: US 12,258,336 B2
(45) Date of Patent: Mar. 25, 2025

(54) PREPARATION OF SEIMICARBAZIDE-SENSITIVE AMINE OXIDASE INHIBITOR AND USE THEREOF

(71) Applicant: SHANGHAI ENNOVABIO PHARMACEUTICALS CO., LTD., Shanghai (CN)

(72) Inventors: Shengyang Liu, Shanghai (CN); Jianwen Deng, Shanghai (CN); Zhiyong Feng, Shanghai (CN); Lei Jiang, Shanghai (CN); Zhi Qiao, Shanghai (CN); Ke Shang, Shanghai (CN); Xiaoping Xie, Shanghai (CN); Xueli Xu, Shanghai (CN); Yuan Xu, Shanghai (CN); Haixia Zhao, Shanghai (CN)

(73) Assignee: SHANGHAI ENNOVABIO PHARMACEUTICALS CO., LTD., Shanghai (CN)

( * ) Notice: Subject to any disclaimer, the term of this patent is extended or adjusted under 35 U.S.C. 154(b) by 864 days.

(21) Appl. No.: 17/279,394

(22) PCT Filed: Sep. 25, 2019

(86) PCT No.: PCT/CN2019/107972
§ 371 (c)(1),
(2) Date: Mar. 24, 2021

(87) PCT Pub. No.: WO2020/063696
PCT Pub. Date: Apr. 2, 2020

(65) Prior Publication Data
US 2022/0081426 A1   Mar. 17, 2022

(30) Foreign Application Priority Data
Sep. 25, 2018  (CN) .......................... 201811119234.2

(51) Int. Cl.
*C07D 407/14*   (2006.01)
*C07D 401/04*   (2006.01)
*C07D 471/08*   (2006.01)
*C07D 487/08*   (2006.01)
*C07D 491/107*  (2006.01)

(52) U.S. Cl.
CPC ......... *C07D 407/14* (2013.01); *C07D 401/04* (2013.01); *C07D 471/08* (2013.01); *C07D 487/08* (2013.01); *C07D 491/107* (2013.01)

(58) Field of Classification Search
CPC .. C07D 407/14; C07D 401/04; C07D 471/08; C07D 487/08; C07D 491/107; C07D 403/04; C07D 405/12; C07D 405/14; C07D 451/06; C07D 239/42; C07D 239/47; C07D 401/06; C07D 401/12; C07D 401/14; C07D 409/14; C07D 417/06; C07D 451/14; C07D 487/04; C07D 491/056; C07D 239/34; A61P 25/00; A61P 27/02; A61P 29/00; A61P 35/00; A61P 3/10; A61P 9/10; A61K 31/506

See application file for complete search history.

(56) References Cited

U.S. PATENT DOCUMENTS

| 8,426,587 B2 | 4/2013 | McDonald et al. |
| 9,302,986 B2 | 4/2016 | Deodhar et al. |

FOREIGN PATENT DOCUMENTS

| CN | 101917845 A | 12/2010 |
| CN | 107266332 A | 10/2017 |
| CN | 109251166 A | 1/2019 |
| WO | 2018/028517 A1 | 2/2018 |
| WO | WO 2018/151985 A1 * | 8/2018 | ........... A61K 31/506 |

OTHER PUBLICATIONS

International Search Report mailed Dec. 25, 2020 corresponding to PCT/CN2019/107972 filed Sep. 25, 2019; 4 pages.

* cited by examiner

*Primary Examiner* — Alicia L Otton
*Assistant Examiner* — David M Shim
(74) *Attorney, Agent, or Firm* — Mintz Levin Cohn Ferris Glovsky and Popeo, P.C.

(57) ABSTRACT

Provided are a preparation of semicarbazide-sensitive amine oxidase inhibitor and the use thereof. In particular, disclosed are a compound as shown in formula I, or a stereoisomer or racemate or pharmaceutically acceptable salt thereof. Also disclosed is that the above-mentioned compound can inhibit semicarbazide-sensitive amine oxidase.

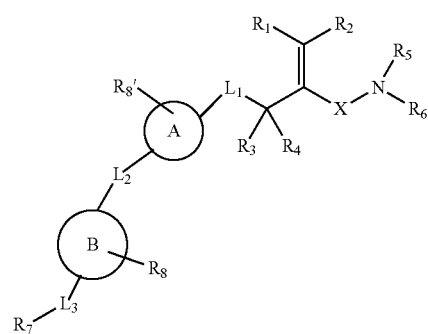

10 Claims, 2 Drawing Sheets
Specification includes a Sequence Listing.

PREPARATION OF SEIMICARBAZIDE-SENSITIVE AMINE OXIDASE INHIBITOR AND USE THEREOF

REFERENCE TO SEQUENCE LISTING

The instant application contains a Sequence Listing, which is being filed electronically in .txt format and is hereby incorporated by reference in its entirety. Said ASCII copy, created on Sep. 25, 2018, is named 050723_567N01US_Sequence_Listing.txt and is 1,723 bytes in size.

FIELD OF THE INVENTION

The present invention relates to the field of pharmaceutical technology, more specifically, relates to a class of semicarbazide-sensitive amine oxidase inhibitors.

BACKGROUND OF THE INVENTION

Semicarbazide-sensitive amine oxidase (SSAO) is a type of amine oxidase containing dopamine quinone groups, which is a member of the semicarbazide-sensitive amine oxidase family and is also called vascular adhesion protein-1, VAP-1 (vascular adhesion protein 1). It is mainly encoded by the AOC3 gene in animals. Smooth muscle cells, adipocytes, and endothelial cells of mammals comprises abundant SSAO, and it is also expressed in various organs such as the vascular, cartilage, and kidney. SSAO in mammals mainly have two isoforms, which are membrane-bound isoform and soluble isoform. The activity of enzymes varies greatly among different species and different tissues of the same species. SSAO can catalyze and metabolize endogenous or food amines into aldehydes, and produce hydrogen peroxide and ammonia. The natural metabolic substrates in the body are mainly aliphatic amines and aromatic amines, wherein methylamine (MA) and aminoacetone are recognized as the two major physiological substrates of SSAO, which are catalyzed into formaldehyde and pyruvaldehyde respectively. In endothelial cells, SSAO exists in the form of vascular adhesion protein-1, which mediates the adhesion of leukocytes to endothelial cells and their exudation.

A large number of studies have confirmed that SSAO and its metabolites are closely related to atherosclerosis, diabetes and complications thereof, obesity, stroke, chronic kidney disease, retinopathy, chronic obstructive pulmonary disease (COPD), autoimmune diseases, multiple sclerosis, rheumatoid arthritis, pain caused by arthritis, Alzheimer's disease and other inflammation-related diseases. It is reported that SSAO/VAP-1 plays an important role in cancer biology. SSAO/VAP-1 small molecule inhibitors inhibit neoangiogenesis and reduce the number of myeloid leukocytes in melanoma and lymphoma. In recent years, studies have also suggested that SSAO plays a role in the occurrence and development of liver diseases such as fatty liver disease. Fatty liver disease may develop into non-alcoholic fatty liver after combination with inflammation and progression, and a certain proportion of patients will further develop into liver fibrosis, cirrhosis and even liver cancer after a period of time.

Given that the function of SSAO plays an important role in the pathological process of various inflammation-related diseases, finding highly effective inhibitors is of great value and significance for controlling diseases caused by SSAO abnormality.

BRIEF SUMMARY OF THE INVENTION

The purpose of the present invention is to provide a class of novel SSAO inhibitors and the preparation and use thereof.

In the first aspect of the present invention, a compound according to Formula I, or stereoisomers or racemates thereof, or pharmaceutically acceptable salts thereof are provided:

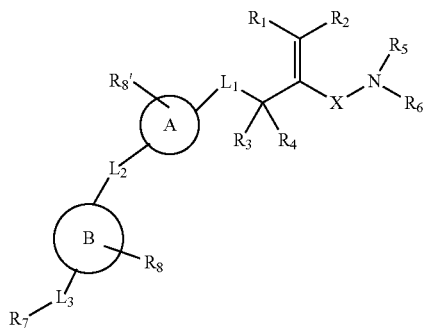

wherein,

A is selected from the group consisting of a substituted or unsubstituted C6-C10 aromatic ring, and substituted or unsubstituted 5-12 membered heteroaromatic ring, or A is a chemical bond (or none);

B is selected from the group consisting of a substituted or unsubstituted C3-10 cycloalkyl, substituted or unsubstituted C6-C10 aromatic ring (including monocyclic ring and fused ring), substituted or unsubstituted 5-12 membered heteroaromatic ring (including monocyclic ring and fused ring), and substituted or unsubstituted 3-12 membered heterocyclic ring (including monocyclic ring, fused ring, bridged ring and spiro ring); wherein, the heteroaromatic ring or heterocyclic ring also contains 1-3 heteroatoms selected from nitrogen, oxygen or sulfur;

$L_1$ is selected from the group consisting of —O—, —NH—, —(C=O)—, —NH(C=O)—, —(C=O)NH—, —NHS(=O)$_2$—, —S(=O)$_2$NH—, and $(CR_9R_{10})_n$; in each of the above groups, when written from left to right, it means that the left side of the group is connected to the A ring, and the right side is connected to —$CR_3R_4$—;

$L_2$ is a chemical bond (or none), or groups selected from the group consisting of —O—, —NH—, —S—, —(C=O)—, —SO$_2$—, —NH—(C=O)—NH—, —NH—S(=O)$_2$—NH—, —(S=O)—, —NH—(S=O)—NH—, —NH—(C=O)—, —(C=O)—NH—, —(CH=CH)$_n$—, —(C≡C)$_n$—, —NH—S(=O)$_2$—, —S(=O)$_2$—NH—, C3-C8 cycloalkyl, 5-8 membered heterocyclyl, and $(CR_9R_{10})_n$;

$L_3$ is selected from the group consisting of a substituted or unsubstituted C3-12 carbocyclic ring (including monocyclic ring, fused ring, bridged ring and spiro ring), substituted or unsubstituted 5-12 membered heterocyclic ring (including monocyclic ring, fused ring, bridged ring and spiro ring), and substituted or unsubstituted 5-6 membered heteroaromatic ring; the heterocyclic ring contains 1-3 heteroatoms selected from nitrogen, oxygen or sulfur;

$R_1$, $R_2$ are each independently selected from the group consisting of H, F and Cl;

R₃, R₄ are each independently selected from the group consisting of H, F, —OH, —CN, substituted or unsubstituted C1-C8-alkyl, substituted or unsubstituted C3-C8 cycloalkyl, substituted or unsubstituted —O—C1-C8 alkyl, substituted or unsubstituted —O—C3-C8 cycloalkyl, substituted or unsubstituted —C6-C10 aryl, substituted or unsubstituted —O—C1-C4 alkyl-C6-C10 aryl, and substituted or unsubstituted —S—C1-C8 alkyl; or R₃ and R₄ together with the carbon atoms to which they are connected constitute a 3-8 membered carbocyclic ring, or 3-8 membered heterocyclic ring; and when L₁ is —O—, —NH—, —(C=O)NH— or —S(=O)₂NH—, neither R₃ nor R₄ is a group selected from the group consisting of —OH, substituted or unsubstituted —O—C1-C8 alkyl, substituted or unsubstituted —O—C3-C8 cycloalkyl, substituted or unsubstituted —O—C1-C4 alkyl-C6-C10 aryl, and substituted or unsubstituted —S—C1-C8 alkyl;

R₅, R₆ are each independently a hydrogen; or R₅ and R₆ together with the nitrogen atom to which they are connected constitute a substituted or unsubstituted 5-6 membered nitrogen-containing heterocyclic ring; or each independently are —NRₐR_b, wherein Rₐ and R_b are each independently H, —C1-C8 alkyl, substituted or unsubstituted C3-C8 cycloalkyl, —C1-C4 alkyl-C6-C10 aryl, or Rₐ and R_b together with the nitrogen atom to which they are connected constitute a 5-6 membered nitrogen heterocyclic ring;

R₇ is selected from the following group: a substituted or unsubstituted groups selected from the group consisting of C5-C6 cycloalkyl, 5-6 membered heterocyclic ring containing 1 nitrogen atom, 4-6 membered heterocyclic ring containing 1 oxygen atom, C1-C6 fluoroalkoxyl, (C1-C6 alkoxyl)C1-C6 alkoxyl, C1-C6 alkylcarbonyl, C2-C6 acylamino, (C1-C6 alkyl)NH—, and (C1-C6 alkyl)(C1-C6 alkyl)N—; the substituted means that the groups being substituted by a group selected from the group consisting of a C1-C6 alkoxyl, C1-C6 alkylcarbonyl, 5-12 membered heteroaromatic ring (monocyclic, fused ring, or condensed ring), and C6-C12 aromatic ring (monocyclic, fused ring, condensed ring);

or R₇ is selected from the group consisting of H, substituted or unsubstituted C1-C6 alkoxyl, and L₃ is selected from the group consisting of a substituted or unsubstituted 5-12 membered bridged ring, and 5-12 membered oxygen-containing spiro heterocyclic ring;

R₈ and R₈' are each independently selected from the group consisting of H, F, Cl, Br, —NO₂, —OH, —CN, substituted or unsubstituted C1-C8-alkyl, substituted or unsubstituted C3-C8 cycloalkyl, substituted or unsubstituted —O—C1-C8 alkyl, substituted or unsubstituted —O—C3-C8 cycloalkyl, substituted or unsubstituted —C6-C10 aryl, substituted or unsubstituted —O—C1-C4 alkyl-C6-C10 aryl, substituted or unsubstituted —S—C1-C8 alkyl, —NRₐR_b, —NHR_c, —SO₂—(C1-C8 alkyl), and —CONRₐR_b; wherein Rₐ and R_b are each independently H, —C1-C8 alkyl, —C1-C4 alkyl-C6-C10 aryl, or Rₐ and R_b together with the nitrogen atom to which they are connected constitute a 5-6 membered nitrogen heterocyclic ring; R_c is selected from the group consisting of —C(=O)—(C1-C8 alkyl), and —C(=O)—(C6-C10 aryl);

R₉, R₁₀ are each independently selected from the group consisting of H, C1-C8 alkyl, —O—C1-C8 alkyl, —O—C3-C8 cycloalkyl, —C6-C10 aryl, —O—C1-C4 alkyl-C6-C10 aryl, —S—C1-C8 alkyl, —CF₃, —S—CF₃, —OCF₃, —OCH₂CF₃, F, —OH, and —CN; or R₉ and R₁₀ together with the carbon atom to which are connected constitute a group selected from the group consisting of a C3-C8 cycloalkyl, and 5-12 membered heterocyclyl;

X is selected from the group consisting of —(C=O)—, —(C=O)—NH—, and —CR₁₁R₁₂;

R₁₁, R₁₂ are each independently selected from the group consisting of H, F, —OH, —CN, substituted or unsubstituted C1-C8-alkyl, substituted or unsubstituted C3-C8 cycloalkyl, substituted or unsubstituted —O—C1-C8 alkyl, substituted or unsubstituted —O—C3-C8 cycloalkyl, substituted or unsubstituted —C6-C10 aryl, substituted or unsubstituted —O—C1-C4 alkyl-C6-C10 aryl, and substituted or unsubstituted —S—C1-C8 alkyl; or R₁₁ and R₁₂ together with the carbon atoms to which they are connected constitute a 3-8 membered carbocyclic ring, or 3-8 membered heterocyclic ring;

with the proviso that the above groups constitute a chemically stable structure;

unless otherwise specified, the above-mentioned "substituted" means one or more hydrogen atoms on the group being substituted by a substituent selected from the group consisting of oxo (=O), hydroxyl, substituted or unsubstituted C5-C6 cycloalkyl, substituted or unsubstituted 5-6 membered heterocyclic ring containing 1 nitrogen atom, 4-6 membered heterocyclic ring containing 1 oxygen atom, C1-C6 alkyl, C1-C6 alkoxyl, C1-C6 fluoroalkoxyl, C1-C6 alkoxyl-C1-C6 alkoxyl, C1-C6 alkylcarbonyl, C2-C6 acylamino, C1-C6 alkyl NH—, (C1-C6 alkyl)(C1-C6 alkyl)N—; the substitution means that above group being substituted by a group selected from the group consisting of C1-C6 alkoxyl and C1-C6 alkylcarbonyl.

In another preferred example, the 5-12 membered oxygen-containing spiro ring heterocycle is a spiro ring selected from the group consisting of oxygen-containing spiro[3,3] ring, oxygen-containing spiro[3,4] ring, oxygen-containing spiro[3,5] ring, oxygen-containing spiro[3,6] ring, and oxygen-containing spiro[4,5] ring.

In another preferred example, L₃ is a structure selected from the group consisting of iperazine ring,

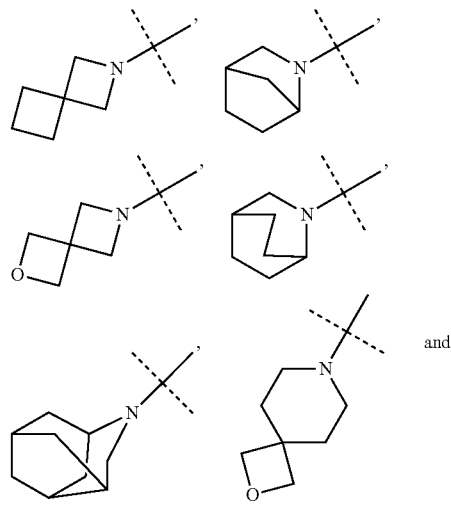

and

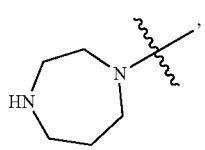

while L₃ can be substituted or unsubstituted.

In another preferred example, the compound of Formula I has a structure shown in the following formula:

II

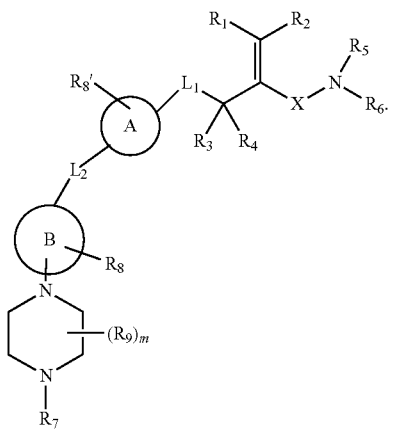

wherein, m is 0, 1, 2, 3, or 4.

In another preferred example, $R_7$ is selected from the group consisting of substituted or unsubstituted C5-C6 cycloalkyl, 5-6 membered heterocyclic ring containing 1 nitrogen atom, 4-6 membered heterocyclic ring containing 1 oxygen atom, 5-12 membered heteroaromatic ring (monocyclic, fused ring, or condensed ring); or $R_7$ is selected from the group consisting of H, substituted or unsubstituted C1-C6 alkoxyl, and L₃ is selected from the group consisting of substituted or unsubstituted 5-12 membered bridged ring, and 5-12-membered oxygen-containing spiro heterocyclic ring.

In another preferred example, $R_7$ is selected from the group consisting of

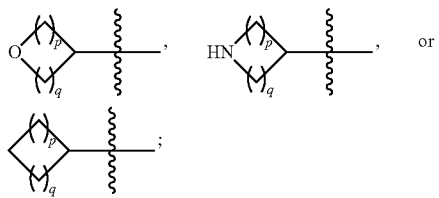

wherein, the p and q are each independently selected from the group consisting of 0, 1, 2, 3 and 4, and the sum of p and q≥1.

In another preferred example, the compound is selected from the following group:

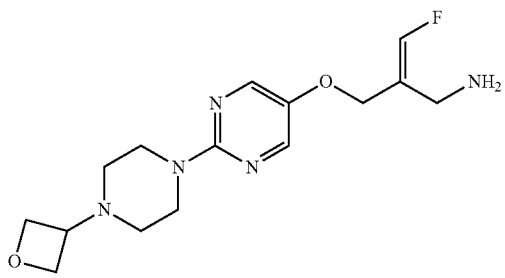

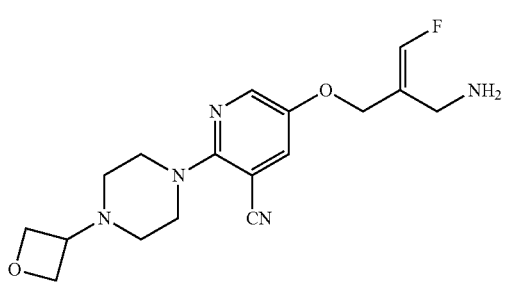

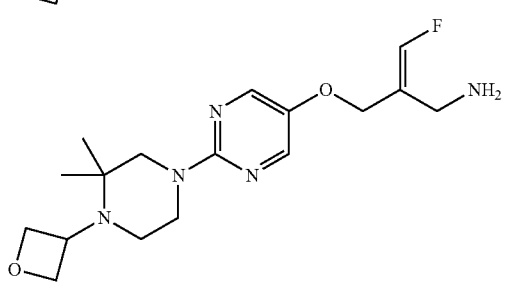

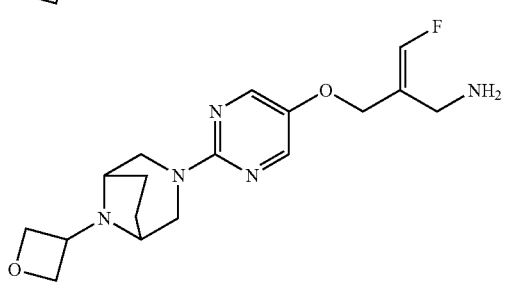

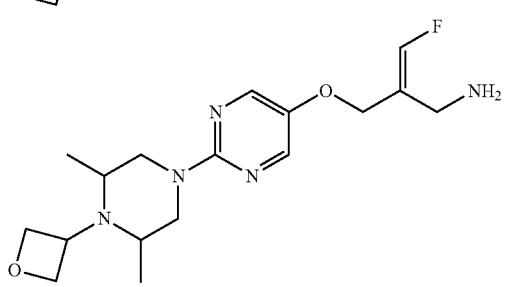

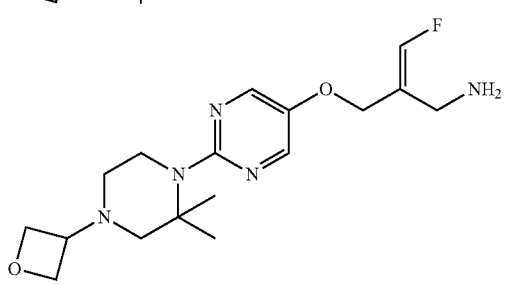

In another referred example, the compound is selected from the following group:
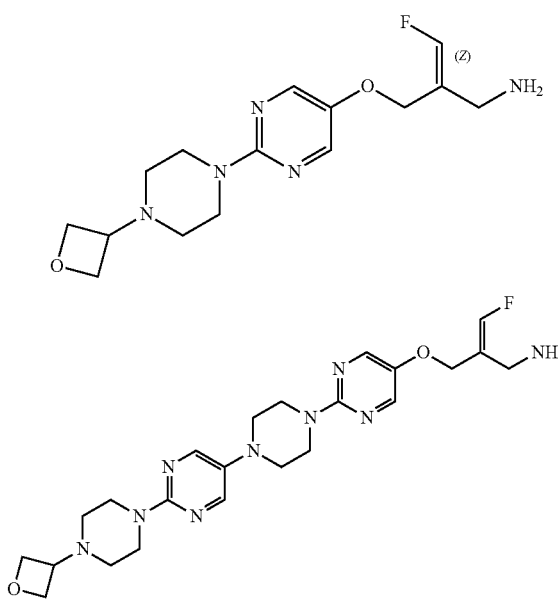

| Compound number | Compound structure |
|---|---|
| 9 | [Structure: pyrimidine-O-CH2-C(=CHF)-CH2-NH2, linked via piperazine-pyrimidine-piperazine-oxetane] |
| 10 | [Structure: pyrimidine-O-CH2-C(=CHF)-CH2-NH2, with gem-dimethyl piperazine-N-oxetane] |
| 11 | [Structure: pyrimidine-O-CH2-C(=CHF)-CH2-NH2, with 2-oxa-6-azaspiro[3.3]heptane] |
| 12 | [Structure: pyrimidine-O-CH2-C(=CHF)-CH2-NH2, with methoxy-bicyclic azabicyclic group] |

In the second aspect of the present invention, a pharmaceutical composition is provided, comprising therapeutically effective amount of a compound according to the first aspect of the present invention, or stereoisomers or racemates thereof, or pharmaceutically acceptable salts thereof, and a pharmaceutically acceptable excipient.

In another preferred example, the pharmaceutical composition is used for preventing and/or treating diseases related to SSAO or regulated by SSAO/VAP-1 protein; preferably, the diseases are selected from the group consisting of inflammatory diseases and/or inflammation-related diseases, diabetes and/or diabetes-related diseases, mental disorders, ischemic diseases, vascular diseases, ocular diseases, fibrosis, neuroinflammatory diseases, cancer, pain-related diseases or tissue transplant rejection.

In another preferred example, the inflammatory diseases and/or inflammation-related diseases are selected from the group consisting of arthritis (including juvenile rheumatoid arthritis) and pain caused by arthritis, Crohn's disease, ulcerative colitis, inflammatory bowel disease (eg., irritable bowel syndrome), psoriasis, asthma, pneumonia, chronic obstructive pulmonary disease (COPD), bronchiectasis, skin inflammation, ocular disease, contact dermatitis, hepatitis, liver autoimmune disease, autoimmune hepatitis, primary biliary cirrhosis, sclerosing cholangitis, autoimmune cholangitis, alcoholic liver disease, atherosclerosis, chronic heart failure, congestive heart failure, ischemic disease, stroke and complications thereof, myocardial infarction and complications thereof, inflammatory cell destruction after stroke, synovitis, systemic inflammatory sepsis, etc.

In another preferred example, the pain is selected from the group consisting of muscle pain, bone and arthrosis pain, neuropathic pain, pain caused by tumor, low back pain, inflammatory pain etc.

In another preferred example, the ocular diseases are uveitis or macular degeneration.

In another preferred example, the fibrosis is selected from the group consisting of cystic fibrosis, idiopathic pulmonary fibrosis, liver fibrosis, including non-alcoholic fatty liver disease such as non-alcoholic steatohepatitis (NASH) and alcohol-induced fibrosis causing liver cirrhosis, renal fibrosis, scleroderma, radiation-induced fibrosis, and complications caused by fibrosis.

In another preferred example, the neuroinflammatory diseases are selected from the group consisting of stroke, Parkinson's disease, Alzheimer's disease, vascular dementia, multiple sclerosis, chronic multiple sclerosis, etc.

In another preferred example, the cancer is selected from the group consisting of lung cancer, breast cancer, colorectal cancer, anal cancer, pancreatic cancer, prostate cancer, ovarian cancer, liver and bile duct cancer, esophageal cancer, non-Hodgkin Lymphoma, bladder cancer, uterine cancer, glioma, glioblastoma, medulloblastoma and other brain tumors, kidney cancer, head and neck cancer, stomach cancer, multiple myeloma, testicular cancer, germ cell tumor, neuroendocrine tumor, cervical cancer, benign tumors of the gastrointestinal tract, breast and other organs, signet ring cell carcinoma, mesenchymal cell tumors including sarcoma, fibrosarcoma, hemangioma, angiomatosis, hemangiopericytoma, pseudoangiomatous stromal hyperplasia, myofibroblastoma, fibromatosis, inflammatory myofibroblastoma, lipoma, angiolipoma, granulosa cell tumor, fibroneuronoma, schwannoma, angiosarcoma, liposarcoma, rhabdomyosarcoma, osteosarcoma, leiomyoma or leiomyosarcoma.

In another preferred example, the diabetes and/or diabetes-related diseases are type I diabetes, type II diabetes, syndrome X, diabetic retinopathy, diabetic nephropathy, diabetic neuropathy or diabetic macular edema.

In another preferred embodiment, the psychiatric disorders are severe depression, bipolar depression or attention deficit hyperactivity disorder.

In another preferred example, the ischemic diseases are stroke and/or complications thereof, myocardial infarction and/or complications thereof, or damage to tissues by inflammatory cells after stroke.

In another preferred example, the vascular diseases are atherosclerosis, chronic heart failure or congestive heart failure.

In another preferred example, the arthritis is osteoarthritis, rheumatic arthritis, rheumatoid arthritis or juvenile rheumatoid arthritis.

In another preferred example, the systemic inflammatory syndrome is systemic inflammatory sepsis.

In another preferred example, the inflammatory bowel disease is irritable bowel disease.

In another preferred example, the liver diseases are liver autoimmune disease, autoimmune hepatitis, primary biliary cirrhosis, sclerosing cholangitis, autoimmune cholangitis, alcoholic liver disease or non-alcoholic fatty liver disease.

In another preferred example, the respiratory diseases are asthma, acute lung injury, acute respiratory distress syndrome, lung inflammation, chronic obstructive pulmonary disease, bronchitis or bronchiectasis.

In another preferred example, the ocular diseases are uveitis, iritis, retinitis, autoimmune ocular inflammation, inflammation or macular degeneration caused by angiogenesis and/or lymphogenesis.

In another preferred example, the skin diseases are contact dermatitis, skin inflammation, psoriasis or eczema.

In another preferred example, the neuroinflammatory diseases are Parkinson's disease, Alzheimer's disease, vascular dementia, multiple sclerosis or chronic multiple sclerosis.

In another preferred example, the non-alcoholic fatty liver diseases are non-alcoholic simple fatty liver, non-alcoholic steatohepatitis, non-alcoholic fatty liver disease-related cryptogenic liver cirrhosis, or primary liver cancer.

In the third aspect of the present invention, the use of the compound according to the first aspect of the present invention, or stereoisomers or racemates thereof, or pharmaceutically acceptable salts thereof, or the pharmaceutical composition according to the second aspect of the present invention is provided, wherein, it is used for the preparation of drugs on preventing and/or treating diseases related to SSAO or regulated by SSAO/VAP-1 protein or activity.

In another preferred example, the diseases related to SSAO or regulated by the SSAO/VAP-1 protein or activity are selected from the group consisting of inflammatory diseases and/or inflammation-related diseases, diabetes and/or diabetes related diseases, mental disorders, ischemic diseases, vascular diseases, ocular diseases, fibrosis, neuroinflammatory diseases, cancer, fibrosis or tissue transplant rejection.

In one embodiment of the method and use of the present invention, the diseases are diabetes-induced diseases selected from diabetic nephropathy, glomerulosclerosis, diabetic retinopathy, non-alcoholic fatty liver disease, and choroidal neovascularization.

In another embodiment of the method and use of the present invention, the diseases are neuroinflammatory diseases. In other embodiments of the methods and uses of the present invention, the diseases are selected from liver fibrosis, liver cirrhosis, renal fibrosis, idiopathic pulmonary fibrosis, and radiation-induced fibrosis. In other embodiments of the method and use of the invention, the disease is cancer.

It should be understood that, within the scope of the present invention, the above-mentioned technical features herein and the technical features specifically described in the following (such as the examples) can be combined with each other, thereby constituting new or preferred technical solutions which need not be specified again herein.

EMBODIMENTS FOR CARRYING OUT THE INVENTION

Figure 1:
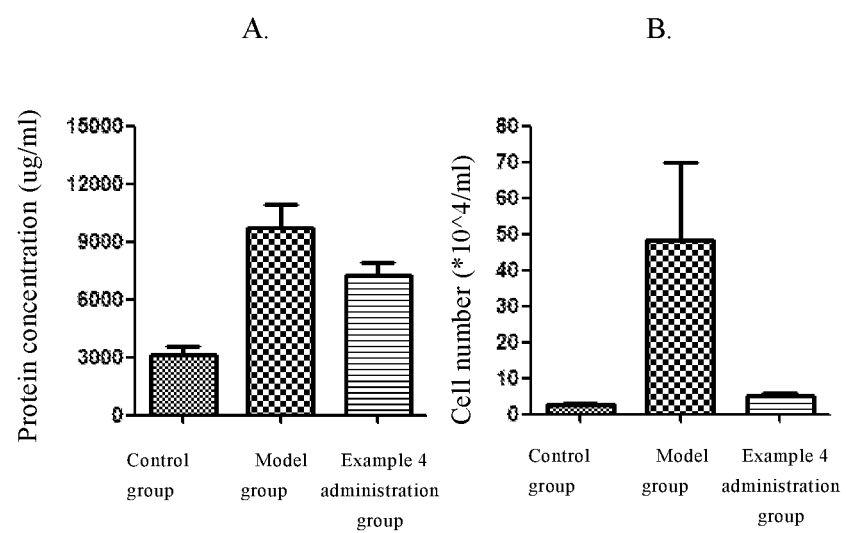
FIG. 1 shows the pharmacodynamic study results of the SSAO compounds in the biological test Example 6 in the ocular inflammation-related disease model.

The inventor discovered a class of SSAO small molecule inhibitors after extensive and in-depth research for the first time. The present invention was complete on this basis.

Terms

Unless otherwise defined, all technical and scientific terms used herein have the same meaning as commonly understood by one of ordinary skill in the art to which this invention belongs.

As used herein, the terms "containing" or "comprising (including)" can be open form, semi-closed form, and closed form. In other words, the terms also include "substantially consisting of" or "consisting of".

As used herein, the term "alkyl" refers to a fully saturated straight or branched hydrocarbon chain group consisting of only carbon and hydrogen atoms and connected to the rest of the molecule by a single bond; having, for example, 1 to 12 (preferably 1 to 8, more preferably 1 to 6) carbon atoms, such as but not limited to methyl, ethyl, n-propyl, iso-propyl, n-butyl, iso-butyl, sec-butyl, tert-butyl, n-pentyl, 2-methylbutyl, 2,2-dimethylpropyl, n-hexyl, heptyl, 2-methylhexyl, 3-methylhexyl, octyl, nonyl and decyl and the like. For the purpose of the present invention, the term "C1-C6 alkyl" refers to alkyl groups containing 1 to 6 carbon atoms.

As used herein, the term "alkoxyl" refers to alkyloxy. The alkyl group is as defined above.

As used herein, the term "cycloalkyl" refers to cyclic alkyl groups consisting only of carbon atoms and hydrogen atoms. For example, including but not limited to cyclopropyl, cyclobutyl, cyclopentyl, cyclohexyl, etc., the cycloalkyl group may optionally have condensed ring, spiro ring or bridged ring structure. "C3-C5 cycloalkyl" refers to cyclic alkyl groups having 3 to 5 carbon atoms; "C5-C6 cycloalkyl" refers to cyclic alkyl groups having 5 to 6 carbon atoms.

The term "5-12 membered heterocyclyl" or "5-12 membered heterocyclic ring" as a group or part of other groups herein refers to stable 5- to 12-membered non-aromatic cyclic groups composed of carbon atoms and 1 to 3 heteroatoms selected from nitrogen, oxygen, sulfur. Unless otherwise specified in the specification, the heterocyclyl may be monocyclic, bicyclic, tricyclic or more ring system, which may include fused ring system, bridged ring system or spiro ring system; nitrogen, carbon or sulfur atoms in the heterocyclic group can be optionally oxidized; nitrogen atoms can be optionally quaternized; heterocyclyl can be partially or fully saturated. The heterocyclyl can be connected to the rest of the molecule through single bond via carbon atom or heteroatom. In heterocyclyl containing fused rings, one or more rings may be aryl or heteroaryl as defined below, provided that the junction to the rest of the molecule is non-aromatic ring atoms. Examples of heterocyclic groups include, but are not limited to: tetrahydropyrrolyl, morpholinyl, piperazinyl, piperidinyl, thiomorpholinyl, 2,7-diaza-spiro[3.5] nonane-7-yl, 2-oxa-6-aza-spiro[3.3]heptane-6-yl, 2,5-diaza-bicyclo[2.2.1]heptan-2-yl, azetidinyl, pyranyl, tetrahydropyranyl, thiopyranyl, tetrahydrofuranyl, oxazinyl, dioxanyl, tetrahydroisoquinolinyl, decahydroisoquinolinyl, imidazolinyl, imidazolidinyl, quinazinyl, thiazolidinyl, isothiazolidinyl, isoxazolidinyl, indoline, octahydroindolyl, octahydroisoindolyl, pyrrolidinyl, pyrazolidinyl, phthalimido, etc.

As used herein, the term "5-6 membered heterocyclic ring containing 1 nitrogen atom" refers to 5- or 6-membered heterocyclic rings containing only one nitrogen atom in the ring.

As used herein, the term "4-6 membered heterocyclic ring containing 1 oxygen atom" refers to 4-membered, 5-membered or 6-membered heterocyclic rings containing only one oxygen atom in the ring.

As used herein, the term "5-6 membered aromatic ring" refers to 5- or 6-membered aromatic rings.

As used herein, the term "5-6 membered heteroaromatic ring" refers to 5- or 6-membered aromatic rings having 1-3 heteroatoms selected from nitrogen, sulfur, and oxygen.

As used herein, the term "halo" refers to fluoro, chloro, bromo or iodo.

The Compounds of the Present Invention

The compounds of the present invention are the compound according to Formula I, or stereoisomers or racemates thereof, or pharmaceutically acceptable salts thereof.

The compounds of the present invention may contain one or more chiral carbon atoms, and therefore can produce enantiomers, diastereomers and other stereoisomeric forms. Each chiral carbon atom can be defined as (R)- or (S)-based on stereochemistry. The present invention intend to include all possible isomers, as well as racemates and optically pure forms thereof. For the preparation of the compounds herein, racemates, diastereomers or enantiomers can be selected as raw materials or intermediates. Optically active isomers can be prepared using chiral synthons or chiral reagents, or resolved using conventional techniques, such as crystallization and chiral chromatography, etc.

Conventional techniques for preparing/separating individual isomers include chiral synthesis from suitable optically pure precursors, or resolution of racemates (or racemates of salts or derivatives) using, for example, chiral high performance liquid chromatography, see for example Gerald Gubitz and Martin G. Schmid (Eds.), Chiral Separations, Methods and Protocols, Methods in Molecular Biology, Vol. 243, 2004; A. M. Stalcup, Chiral Separations, Annu. Rev. Anal. Chem. 3:341-63, 2010; Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816: Heller, Acc. Chem. Res. 1990, 23, 128.

The term "pharmaceutically acceptable salts" include pharmaceutically acceptable acid addition salts and pharmaceutically acceptable base addition salts.

"Pharmaceutically acceptable acid addition salts" refer to salts formed with inorganic acid or organic acid that can retain the biological effectiveness of the free base without other side effects. Inorganic acid salts include, but are not limited to, hydrochloride, hydrobromide, sulfate, nitrate, phosphate, etc.; organic acid salts include, but are not limited to, formate, acetate, 2,2-dichloroacetate, trifluoroacetate, propionate, caproate, caprylate, caprate, undecylenate, glycolate, gluconate, lactate, sebacate, adipate, glutarate, malonate, oxalate, maleate, succinate, fumarate, tartrate, citrate, palmitate, stearate, oleate, cinnamate, laurate, malate, glutamate, pyroglutamate, aspartate, benzoate, methanesulfonate, benzenesulfonate, p-toluenesulfonate, alginate, ascorbate, salicylate, 4-aminosalicylate, naphthalenedisulfonate, etc. These salts can be prepared by methods known in the art.

"Pharmaceutically acceptable base addition salts" refer to salts formed with inorganic base or organic base that can maintain the biological effectiveness of the free acid without other side effects. Salts derived from inorganic bases include, but are not limited to, sodium, potassium, lithium, ammonium, calcium, magnesium, iron, zinc, copper, manganese, aluminum, and the like. Preferred inorganic salts are ammonium, sodium, potassium, calcium and magnesium salts. Salts derived from organic bases include, but are not limited to the following salts: primary amines, secondary amines and tertiary amines, substituted amines including natural substituted amines, cyclic amines and basic ion exchange resins, such as ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, dicyclohexylamine, lysine, arginine, histidine, caffeine, procaine, choline, betaine, ethylenediamine, glucosamine, methylglucosamine, theobromine, purine, piperazine, piperidine, N-ethylpiperidine, polyamine resin, etc. Preferred organic bases include isopropylamine, diethylamine, ethanolamine, trimethylamine, dicyclohexylamine, choline and caffeine. These salts can be prepared by methods known in the art.

Preparation Method

The following reaction scheme exemplarily illustrate the method for preparing the compound of Formula I, or stereoisomer or racemate thereof, or pharmaceutically acceptable salts thereof, wherein each group is as described above. It should be understood that combinations of substituents and/or variables in the formula are permissible only when such combinations result in stable compounds in the following reaction schemes. It should also be understood that other formula can be prepared by those skilled in the field of organic chemistry by the methods disclosed herein (by applying appropriately substituted starting materials and modifying the synthesis parameters as needed using methods well known to those skilled in the art) or known methods.

Those skilled in the art should also understand that some functional groups of the intermediate compounds may need to be protected by appropriate protecting groups in the methods described below. Such functional groups include hydroxyl, amino, mercapto and carboxylic acid. Suitable hydroxy protecting groups include trialkylsilyl or diarylalkylsilyl (e.g. tert-butyldimethylsilyl, tert-butyldiphenylsilyl or trimethylsilyl), tetrahydropyranyl, benzyl, etc. Suitable protecting groups for amino, amidino and guanidino include tert-butoxycarbonyl, benzyloxycarbonyl, etc. Suitable protecting groups for sulfhydryl include —C(O)—R" (wherein R" is alkyl, aryl or aralkyl), p-methoxybenzyl, trityl, etc. Suitable carboxy protecting groups include alkyl, aryl or aralkyl esters.

Protecting groups can be introduced and removed according to standard technique known to those skilled in the art and as described herein. The use of protecting groups has been described in Greene, T. W. and P. G. M. Wuts, Protective Groups in Organic Synthesis, (1999), 4th Ed., Wiley in detail. The protecting groups can also be polymer resins.

Application

The compounds of the present invention have excellent SSAO inhibitory activity and can be used in a pharmaceutical composition with the compounds of the present invention as active ingredient for preventing and/or treating diseases related to SSAO or regulated by SSAO/VAP-1 protein, such as atherosclerosis, diabetes and complications thereof, obesity, stroke, chronic kidney disease, chronic obstructive pulmonary disease (COPD), autoimmune disease, multiple sclerosis, rheumatoid arthritis, pain caused by arthritis, Alzheimer's disease, ocular disease, liver disease (such as fatty liver, hepatitis, liver fibrosis, liver cirrhosis, liver cancer).

In the application, the term "pharmaceutical composition" refers to preparations of the compounds of the present invention and medium generally accepted in the art for the delivery of biologically active compounds to mammals (such as human). The medium include a pharmaceutically acceptable carrier. The purpose of the pharmaceutical composition is to promote the administration of the organism, which is beneficial to the absorption of the active ingredient and thus exerting biological activity.

In the application, the term "pharmaceutically acceptable" refers to a substance (such as carriers or diluents) that does not affect the biological activity or properties of the compound, and is relatively non-toxic, that is, the substance can be administered to individuals without causing undesirable biological reactions or interactions with any components included in the composition in an undesirable manner.

In the application, the term "pharmaceutically acceptable excipients" include, but is not limited to any adjuvants, carriers, excipients, glidants, sweeteners, diluents, preservatives, dyes/colorants, flavors, surfactants, wetting agents, dispersants, suspending agents, stabilizers, isotonic agents, solvents or emulsifiers as acceptable for human or livestock use approved by relevant government authorities.

In the application, the terms "preventive", "prevention" and "preventing" include reducing the possibility of the ocular occurring or deterioration in patients.

In the application, the term "treatment" and other similar synonyms include the following meanings:
(i) preventing the occurrence of disease or condition in mammals, especially when such mammals are susceptible to the disease or condition, but has not been diagnosed as suffering the disease or condition;
(ii) inhibiting disease or condition, that is, curbing the development;
(iii) relieving disease or condition, that is, retreating the state of disease or condition; or
(iv) easing the symptoms caused by the disease or condition.

In the application, the term "effective amount", "therapeutically effective amount" or "pharmaceutical effective amount" refers to the amount of at least one agent or compound, which is sufficient to relieve one or more symptoms of the disease or condition treated to some extent after administration. The result can be the reduction and/or alleviation of signs, symptoms or causes, or any other desired changes in the biological system. For example, the "effective amount" for treatment is the amount of the composition containing the compound disclosed herein required to provide significant disease relief clinically. Techniques such as dose escalation tests can be used to determine the effective amount suitable for any individual case.

In the application, the terms "administration", "administrate", "administrating" and the like refer to methods capable of delivering compounds or compositions to desired site for biological action. These methods include, but are not limited to, oral route, transduodenal route, parenteral injection (including intravenous, subcutaneous, intraperitoneal, intramuscular, intra-arterial injection or infusion), topical administration, and rectal administration. Those skilled in the art are familiar with administration technique that can be used for the compounds and methods described herein, for example those discussed in Goodman and Gilman, The Pharmacological Basis of Therapeutics, current ed.; Pergamon; and Remington's, Pharmaceutical Sciences (current edition), Mack Publishing Co., Easton, Pa. In a preferred embodiment, the compounds and compositions discussed herein are administered orally.

In the application, the terms "drug combination", "drugs of combined use", "combination drug", "administration of other treatments", "administration of other therapeutic agents", etc. refer to medical treatment obtained by mixing or combining more than one active ingredient, which includes fixed and non-fixed combinations of active ingredients. The term "fixed combination" refers to the simultaneous administration of at least one compounds described herein and at least one synergistic agents to patients in the form of single entity or single dosage form. The term "non-fixed combination" refers to the simultaneous administration, combined administration or sequential administration at variable intervals of at least one compounds described herein and at least one synergistic agents to patient in the form of separate entities. These also apply to cocktail therapy, such as the administration of three or more active ingredients.

The relative inhibitory efficacy of the compounds can be measured by the amount required to inhibit the SSAO/VAP-1 amine oxidase activity in a variety of ways, for example, in vitro tests using recombinant human protein or recombinant non-human enzymes, cellular tests using cells expressing normal rodent enzymes, tests on cells transfected with human protein, in vivo tests in rodents and other mammals, etc.

The methods for inhibiting SSAO/VAP-1 in patients suffering from inflammatory diseases and treating inflammatory diseases using the compounds described by Formula I and II are also disclosed. Human inflammatory diseases include arthritis and pain caused by arthritis, Crohn's disease, irritable bowel syndrome, psoriasis, asthma, chronic obstructive pulmonary disease, bronchiectasis, joint sclerosis, inflammation caused by diabetes, and inflammatory cell destruction after stroke.

Therefore, in one aspect, the present invention relates to the method for inhibiting amine oxidase in individuals in need thereof. The method comprises administering an effective amount of the compound of Formula I or Formula II to the individual to produce positive therapeutic responses.

In another aspect, the present invention relates to the method for treating diseases associated with amine oxidase. The method comprises administering a therapeutically effective amount of the compound of Formula I or Formula II to individuals in need thereof.

In another aspect, the present invention relates to the method for treating diseases regulated by SSAO/VAP-1. The method comprises administering a therapeutically effective amount of the compound of Formula I or Formula II to individuals in need thereof.

The above method is applicable where the diseases are inflammation. As used herein, "inflammation" includes various indications, including arthritis (including juvenile rheumatoid arthritis), Crohn's disease, ulcerative colitis, inflammatory bowel disease (eg., irritable bowel syndrome), psoriasis, asthma, pneumonia, chronic obstructive pulmonary disease (COPD), bronchiectasis, skin inflammation, ocular disease, contact dermatitis, hepatitis, liver autoimmune disease, autoimmune hepatitis, primary biliary cirrhosis, sclerosing cholangitis, autoimmune cholangitis, alcoholic liver disease, atherosclerosis, chronic heart failure, congestive heart failure, ischemic disease, stroke and complications thereof, myocardial infarction and complications thereof, inflammatory cell destruction after stroke, synovitis, systemic inflammatory sepsis, etc.

The above method is also applicable where the diseases are type I diabetes, type II diabetes and complications thereof.

The above method is also applicable where the diseases are macular degeneration and/or other ocular diseases.

The above method is also applicable where the diseases are fibrosis. As used herein, "fibrosis" includes such diseases like cystic fibrosis, idiopathic pulmonary fibrosis, liver fibrosis, including non-alcoholic fatty liver disease such as non-alcoholic steatohepatitis (NASH) and alcohol-induced fibrosis causing liver cirrhosis, renal fibrosis, scleroderma, radiation-induced fibrosis, and other diseases in which excessive fibrosis contributes to disease pathology.

The above method is also applicable for the treatment of neuroinflammatory diseases. As used herein, "neuritis diseases" include various indications, including stroke, Parkinson's disease, Alzheimer's disease, vascular dementia, multiple sclerosis, chronic multiple sclerosis, etc.

The above method is also applicable to pain-related diseases selected from but not limited to the following group: muscle pain, bone and arthrosis pain, neuropathic pain, pain caused by tumor, lumbago and backache, inflammatory pain etc.

The above method is also applicable or the treatment of cancer. In one embodiment, the cancer is selected from lung cancer, breast cancer, colorectal cancer, anal cancer, pancreatic cancer, prostate cancer, ovarian cancer, liver and bile duct cancer, esophageal cancer, non-Hodgkin Lymphoma, bladder cancer, uterine cancer, glioma, glioblastoma, medulloblastoma and other brain tumors, kidney cancer, head and neck cancer, stomach cancer, multiple myeloma, testicular cancer, germ cell tumor, neuroendocrine tumor, cervical cancer, benign tumors of the gastrointestinal tract, breast and other organs, signet ring cell carcinoma, mesenchymal cell tumors including sarcoma, fibrosarcoma, hemangioma, angiomatosis, hemangiopericytoma, pseudoangiomatous stromal hyperplasia, myofibroblastoma, fibromatosis, inflammatory myofibroblastoma, lipoma, angiolipoma, granulosa cell tumor, fibroneuronoma, schwannoma, angiosarcoma, liposarcoma, rhabdomyosarcoma, osteosarcoma, leiomyoma or leiomyosarcoma.

The present inventions will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, percentage and parts are calculated by weight.

The experimental materials and reagents used in the following examples can be obtained from commercial channels unless otherwise specified.

The synthesis method of the intermediate is as follows:

Example A: tert-Butyl (E)-(2-(bromomethyl)-3-fluoroallyl) carbamate

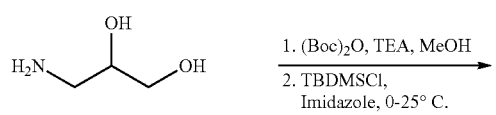

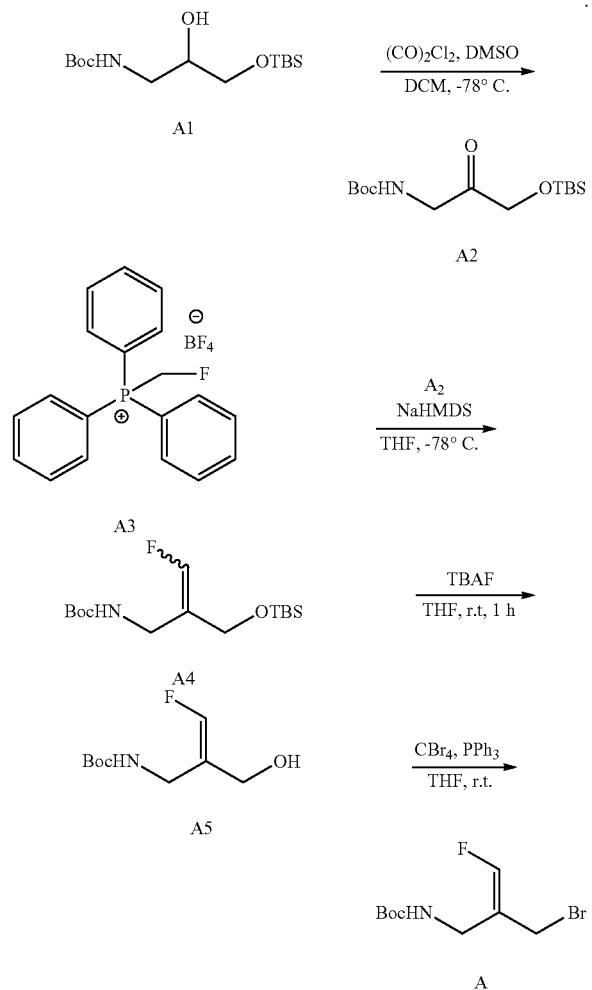

Example A1

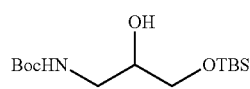

To a stirred solution of 3-aminopropane-1,2-diol (400 g, 4395.6 mmol) and triethylamine (665.9 g, 6593.4 mmol) in methanol (4 L) was added di-tert-butyl dicarbonate (1040.1 g, 4835.2 mmol) at 0-10° C. The reaction solution was stirred at 25° C. for 2 h, concentrated under reduced pressure until no methanol left. The residue was dissolved in dichloromethane (5 L), then imidazole (448.6 g, 6593.4 mmol) was added. At 0-10° C., a solution of TBDMSCl (791.2 g, 5274.7 mmol) in dichloromethane (1 L) was slowly dropped into the above solution. The mixture was stirred at room temperature for 2 h after addition, and 1% citric acid solution (2 L) was added. The organic phase was separated, washed twice with saturated brine, dried over anhydrous sodium sulfate, and evaporated in vacuo to provide a colorless oil. The oil was dissolved in n-heptane (5 L), washed with 5% brine until no imidazole and triethylamine was remained, dried over anhydrous sodium sulfate, and evaporated in vacuo to afford crude product as a colorless oil (1206.6 g, 91%).

Example A2

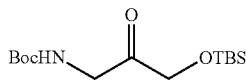

To a solution of oxalyl chloride (203.4 g, 1603.2 mmol) in anhydrous dichloromethane (3000 mL) anhydrous DMSO (158.4 g, 2030.8 mmol) was slowly added under nitrogen atmosphere at −78° C. (note: a large amount of CO and $CO_2$ were released, and the temperature should not exceed −60° C.). After addition, the reaction solution was stirred at −78° C. for 30 minutes, then a solution of compound 1-4 (326.0 g, 1068.8 mmol) in dry dichloromethane (500 mL) was slowly dropped into the reaction solution at −78° C. After addition, the reaction solution was stirred at −78° C. for another 1 hour Triethylamine (545.1 g, 5344.0 mmol) (moisture shall be controlled) was slowly added at −78° C. After addition, the reaction solution was warmed to room temperature, stirred for 1 hour, and monitored by TLC. After starting materials was consumed, water (1000 mL) was added to the reaction solution, and the organic layer was separated and the aqueous layer was extracted with dichloromethane (200 mL*2). The organic layers were combined, dried over anhydrous sodium sulfate and evaporated in vacuo to provide crude product. The crude was dissolved in 3 L of n-heptane, washed with 3% brine until no triethylamine was remained, and purified by distillation to afford the title compound A2 (colorless oil, 225.0 g, 70.1%).

Example A4

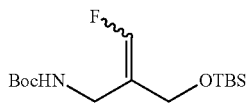

A solution of the compound A3 (438.0 g, 1148.6 mmol) in anhydrous tetrahydrofuran (1000 mL) was slowly dropped into a solution of sodium bis(trimethylsilyl)amide (2M, 1673.0 mL, 3346.0 mmol) in tetrahydrofuran at −68° C. After addition, the reaction solution was stirred at −68° C. for 1 hour, and a solution of compound 1-5 (290.0 g, 956.0 mmol) in tetrahydrofuran (400 mL) was slowly dropped into the reaction and stirred for another 8 hours. The reaction solution was warmed to 0° C., stirred for 2 hours, and monitored by LCMS. After starting materials was consumed, water (1000 mL) was added to the reaction solution and the mixture was extracted with ethyl acetate (500 mL×3). The organic layers were combined, washed with saturated brine (200 mL×2), dried over anhydrous sodium sulfate and evaporated in vacuo to provide crude product. 1 Kg of silica gel was added to the crude product, and eluted with petroleum ether. The eluted liquid was evaporated in vacuo to provide a residue. The residue was distilled under reduced pressure (distillates at 100-110° C. was collected) to afford A4 (light yellow oil, 173.0 g, 46.2%, E/Z=10:1). MS(ESI): m/z=264.15 [M−56+H]$^+$.

Example A5: tert-butyl (E)-(3-fluoro-2-(hydroxymethyl)allyl) carbamate

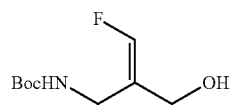 [SMILES: CC(C)(C)OC(=O)NC/C(=C\F)CO]

To the solution of Example A4 (173.0 g, 538.9 mmol, E:Z=10:1) in tetrahydrofuran (400 mL) was added TBAF tetrahydrate (170.0 g, 538.9 mmol) at 0° C. The reaction solution was warmed to room temperature, stirred for 1 hour, and monitored by LCMS. After starting materials were consumed, water (1000 mL) was added to the reaction and the mixture was extracted with ethyl acetate (400 mL×2). The organic layers were combined, washed with 0.1 N aqueous hydrochloric acid (200 mL×2) and saturated brine (100 mL×2), dried over anhydrous sodium sulfate and evaporated in vacuo to provide a crude product. The crude product was purified by distillation under reduced pressure (distillates at 100-120° C. was collected) to afford the title compound A5 (light yellow oil, 104.0 g, 94.2%, E:Z=10:1). $^1$H NMR (400 MHz, CDCl$_3$) δ 6.59 (d, J=83.7 Hz, 1H), 5.01 (br s, 1H), 3.95 (s, 2H), 3.91 (dd, J=6.5, 1.6 Hz, 2H), 3.81 (br s, 1H), 1.43 (s, 9H).

Example A: tert-Butyl (E)-(2-(bromomethyl)-3-fluoroallyl)carbamate

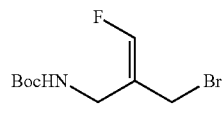

A solution of CBr$_4$ (251.9 g, 761.0 mmol) in anhydrous 1,2-dichloromethane (100 mL) was slowly dropped to solution of Example A5 (104.0 g, 507.3 mmol) and triphenylphosphine (199.4 g, 761.0 mmol) in anhydrous 1,2-dichloromethane (580 mL) at ° C. After dripping, the reaction solution was raised to room temperature and stirred for 30 minutes. The reaction was monitored by LCMS. After starting material in the reaction solution was consumed, the reaction solution was evaporated in vacuo to afford crude product. The crude product was purified by column chromatography (petroleum ether:ethyl acetate=10:1) to afford the title compound A (white solid 104.0 g, E:Z=10:1). It was recrystallized twice with petroleum ether (500 mL) to provide a white solid (85.5 g, 63.2%, E:Z=50:1). $^1$H NMR (400 MHz, CDCl$_3$) δ 6.77 (d, J=81.2 Hz, 1H), 4.76 (brs, 1H), 4.00 (d, J=4.6 Hz, 2H), 3.95 (dd, J=3.4, 0.6 Hz, 2H), 1.45 (s, 9H).

Example 1: (E)-2-(((2-(3,5-Dimethyl-4-(oxbutan-3-yl)piperazin-1-yl) pyrimidin-5-yl)oxo)methyl)-3-fluoroprop-2-en-1-amine

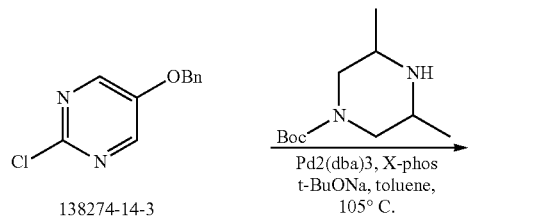

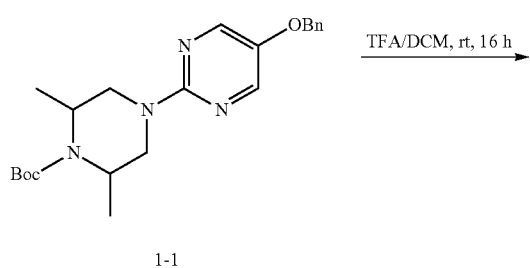

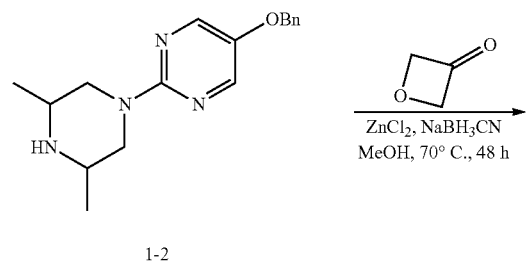

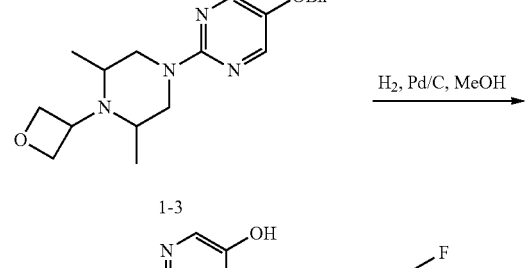

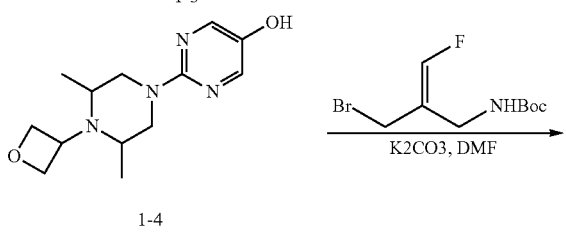

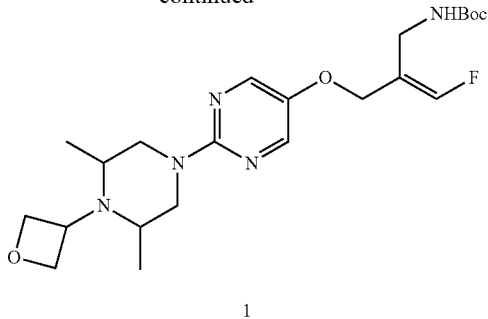

Example 1-1: tert-butyl 4-(5-(benzyloxy)pyrimidin-2-yl)-2,6-dimethylpiperazine-1-carboxylate

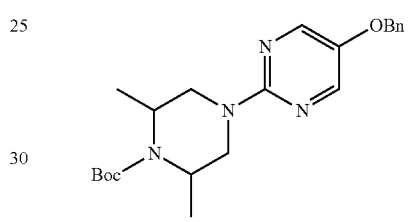

To a solution of compound CAS: 138274-14-3 (220 mg, 1.0 mmol), tert-butyl 3,5-dimethylpiperazine-1-carboxylate (291 mg, 1.5 mmol), sodium tert-butoxide (174 mg, 2.0 mmol) in toluene (3 mL) were added tris(benzylideneacetone)dipalladium(0) (45 mg, 0.05 mmol) and 2-dicyclohexylphosphorus-2,4,6-di-iso-propylbiphenyl (47 mg, 0.1 mmol). The mixture was stirred at 105° C. under nitrogen atmosphere for 1 hour in a sealed tube. The reaction solution was cooled and concentrated. The residue was separated and purified on a silica gel column (dichloromethane:methanol=20:1) to afford the title compound 1-1 (141 mg, 39%) as yellow oil. MS (ESI): m/z=399.2 [M+H]$^+$.

Example 1-2: 5-(benzyloxy)-2-(3,5-dimethylpiperazin-1-yl)pyrimidine

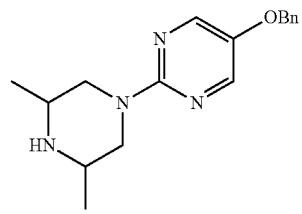 [SMILES: CC1CN(c2ncc(OCc3ccccc3)cn2)CC(C)N1]

Trifluoroacetic acid (0.5 mL) was added to a solution of compound 1-1 (141 mg, 0.35 mmol) in dichloromethane (2 mL). The mixture was stirred at room temperature for 16 hours, concentrated, adjusted to pH=9 with saturated sodium bicarbonate solution. The solution was extracted with ethyl acetate (20 mL×2), dried and concentrated to afford the title compound 1-2 (105 mg, 99%) as a yellow oil. MS (ESI): m/z=299.1 [M+H]$^+$.

Example 1-3: 5-(benzyloxy)-2-(3,5-dimethyl-4-(oxbutan-3-yl)piperazin-1-yl) pyrimidine

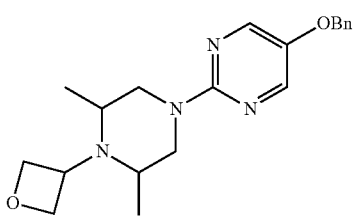 [SMILES: CC1CN(c2ncc(OCc3ccccc3)cn2)CC(C)N1C1COC1]

Zinc chloride in tetrahydrofuran (1 M, 0.52 mL, 0.52 mmol), sodium cyanoborohydride (66 mg, 1.05 mmol) were added to a solution of compound 1-2 (104 mg, 0.35 mmol), 3-oxetanone (126 mg, 1.75 mmol) in methanol (5 mL). The mixture was heated and stirred for 48 hours, then cooled and concentrated. The residue was separated and purified on a silica gel column (petroleum ether:ethyl acetate=13:87) to afford the title compound 1-3 (44 mg, 35%) as a yellow solid. MS (ESI): m/z=355.2 [M+H]$^+$.

Example 1-4: 2-(3,5-dimethyl-4-(oxbutan-3-yl)piperazin-1-yl)pyrimidine-5-phenol

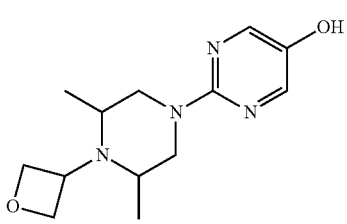 [SMILES: CC1CN(c2ncc(O)cn2)CC(C)N1C1COC1]

Example 1-3 (44 mg, 0.12 mmol) in methanol (5 mL) was placed in a single-neck bottle, and palladium-carbon (20 mg) was added and exchanged for three times with hydrogen balloon. The reaction solution was stirred at room temperature for 1 hour. Palladium-carbon was filtered off, and the filtrate was concentrated to afford the title compound 1-4 (22 mg, 67%) as a yellow oil. MS (ESI): m/z=265.1 [M+H]$^+$.

Example 1-5: tert-butyl(E)-(2-(((2-(3,5-dimethyl-4-(oxbutan-3-yl)piperazin-1-yl)pyrimidine-5-yl)oxo)methyl)-3-fluoroallyl)carbamate

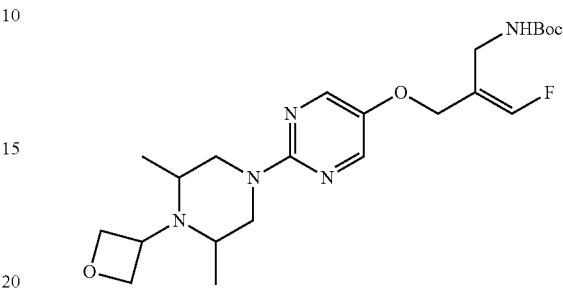

To a solution of Example 1-4 (22 mg, 0.08 mmol), and tert-butyl (E)-(2-(bromomethyl)-3-fluoroallyl) carbamate (26 mg, 0.1 mmol) in N,N-dimethylformamide (2 mL) was added potassium carbonate (17 mg, 0.12 mmol). The mixture was heated to 50° C., and stirred for 1 hour, and then the reaction solution was directly purified on a reverse phase C-18 column (acetonitrile/formic acid aqueous solution) to afford the title compound 1-5 (15 mg, 40%) as a colorless oil. MS (ESI): m/z=452.2 [M+H]$^+$.

Example 1: (E)-2-(((2-(3,5-dimethyl-4-(oxbutan-3-yl)piperazin-1-yl)pyrimidin-5-yl)oxo)methyl)-3-fluoroprop-2-en-1-amine

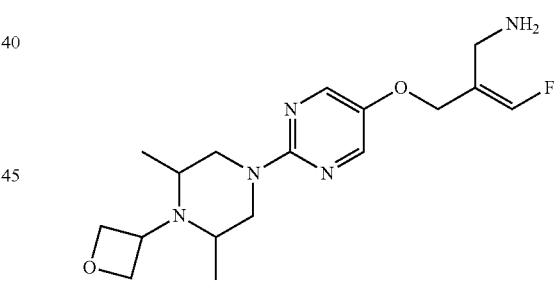

Trifluoroacetic acid (0.5 mL) was added to Example 1-5 (15 mg, 0.033 mmol) in dichloromethane (2 mL). The resulting mixture was stirred at room temperature for 30 minutes, concentrated and adjusted to pH 7-8 with ammonia water, and then the reaction solution was directly purified on reverse phase C-18 column (acetonitrile/ammonium bicarbonate aqueous solution) to afford the title compound 3 (5.5 mg, 47%) as a white solid. MS (ESI): m/z=352.6 [M+H]$^+$.

$^1$H NMR (400 MHz, CD$_3$OD): δ 8.15 (s, 2H), 8.20 (d, J=83.6 Hz, 1H), 4.73 (t, J=6.4 Hz, 2H), 4.54-4.53 (m, 2H), 4.12-4.14 (m, 1H), 3.76-3.72 (m, 2H), 3.57-3.52 (m, 2H), 3.48 (d, J=2.4 Hz, 2H), 2.81-2.73 (m, 2H), 1.04 (d, J=6.4 Hz, 6H).

The following compounds were obtained using a method similar to that in Example 1 by replacing the corresponding starting materials.

| Number | Compound structure | LCMS, NMR |
|---|---|---|
| 2 | 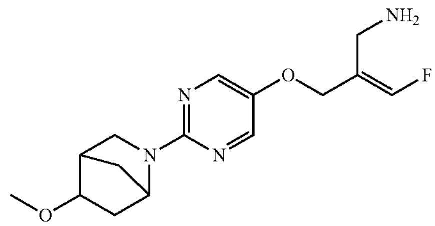 [SMILES: COC1CC2CC1CN2c1ncc(OC/C(=C/F)CN)cn1] | MS (ESI): m/z = 308.9 [M + H]⁺<br>¹H NMR (400 MHz, CDCl₃) δ 8.06 (d, J = 6.1 Hz, 2H), 6.63 (d, J = 82.8 Hz, 1H), 4.57 (s, 1H), 4.41 (dd, J = 3.6, 0.8 Hz, 2H), 3.55 – 3.47 (m, 3H), 3.44 (dd, J = 10.3, 4.0 Hz, 1H), 3.30 (s, 3H), 2.96 (d, J = 10.3 Hz, 1H), 2.73 (s, 1H), 2.01 (ddd, J = 13.3, 6.8, 2.5 Hz, 1H), 1.79 (d, J = 10.1 Hz, 1H), 1.66 (s, 1H), 1.55 (s, 1H). |
| 3 | 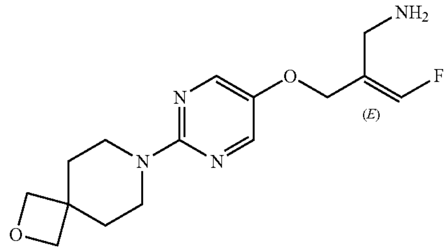 [SMILES: NC/C(=C\F)COc1cnc(N2CCC3(CC2)COC3)nc1] | MS(ESI): m/z = 308.9 [M + H]⁺.<br>¹HNMR (400 MHz, CD₃OD) δ 8.12 (s, 2H), 6.99 (s, 0.5H), 6.78 (s, 0.5H), 4.51 (dd, J = 3.6, 0.9 Hz, 2H), 4.47 (s, 4H), 3.68 – 3.62 (m, 4H), 3.48 (d, J = 2.1 Hz, 2H), 1.88 – 1.82 (m, 4H). |

Example 4: (E)-3-fluoro-2-(((2-(4-(oxbutan-3-yl)piperazin-1-yl)pyrimidin-5-yl)oxo)methyl)prop-2-en-1-amine

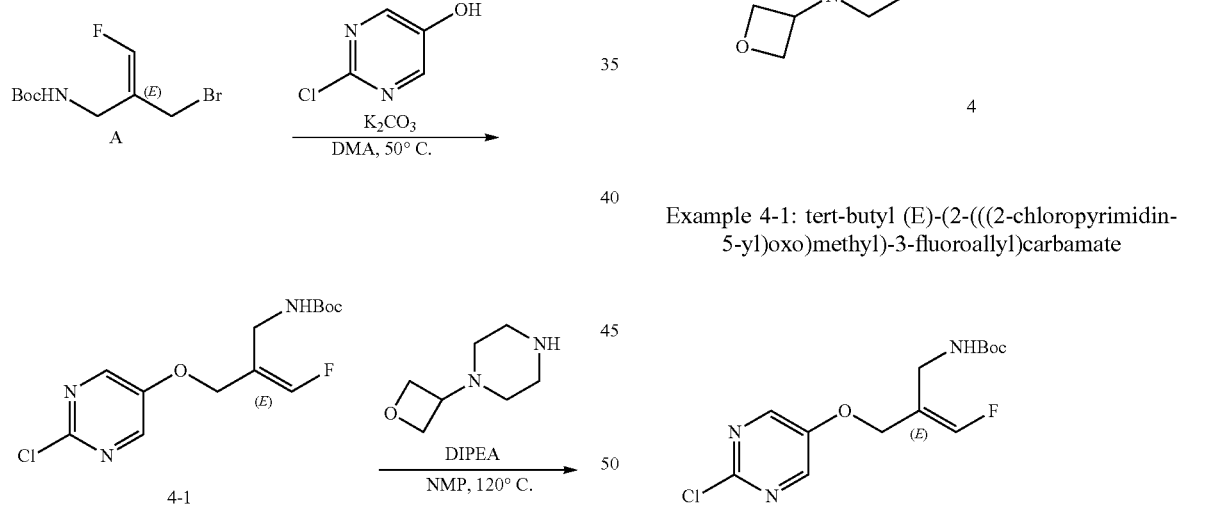

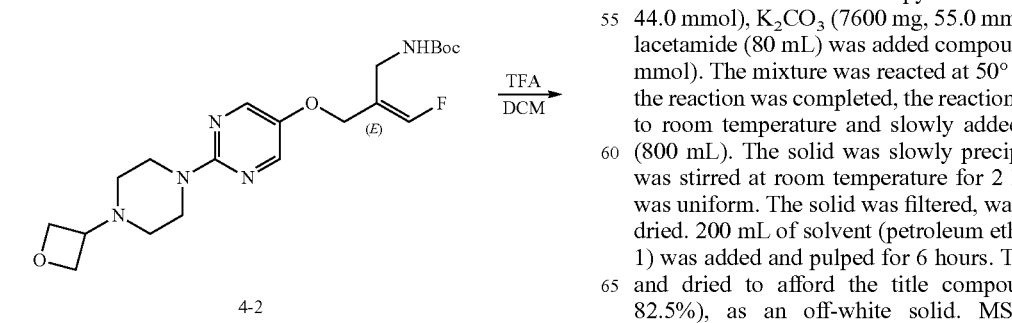

Example 4-1: tert-butyl (E)-(2-(((2-chloropyrimidin-5-yl)oxo)methyl)-3-fluoroallyl)carbamate To a solution of 2-chloropyrimidine-5-phenol (5725 mg, 44.0 mmol), K₂CO₃ (7600 mg, 55.0 mmol) in N,N-dimethylacetamide (80 mL) was added compound A (9800 mg, 36.7 mmol). The mixture was reacted at 50° C. for 3 hours. After the reaction was completed, the reaction solution was cooled to room temperature and slowly added dropwise to water (800 mL). The solid was slowly precipitated. The mixture was stirred at room temperature for 2 hours until the solid was uniform. The solid was filtered, washed with water, and dried. 200 mL of solvent (petroleum ether:ethyl acetate=10:1) was added and pulped for 6 hours. The solid was filtered and dried to afford the title compound 4-1 (9600 mg, 82.5%), as an off-white solid. MS (ESI): m/z=262.0 [M−55]⁺.

Example 4-2: tert-butyl(E)-(3-fluoro-2-(((2-(4-(oxbutan-3-yl)piperazin-1-yl)pyrimidin-5-yl)oxo)methyl)allyl)carbamate Example 4: (E)-3-fluoro-2-(((2-(4-(oxbutan-3-yl)piperazin-1-yl)pyrimidin-5-yl)oxo)methyl)prop-2-en-1-amine

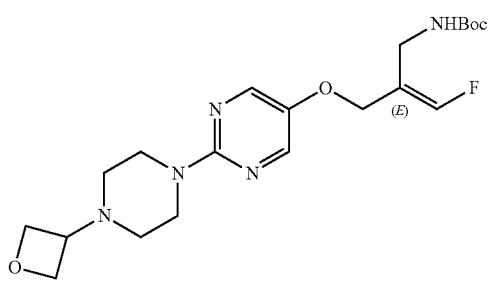 [SMILES: CC(C)(C)OC(=O)NC/C(=C\F)COc1cnc(N2CCN(C3COC3)CC2)nc1]

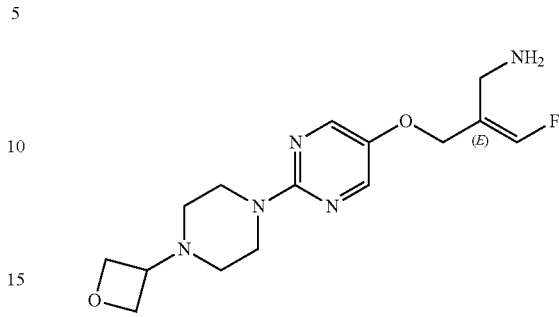

The solution of Example 4-1 (9600 mg, 30.2 mmol) in N-methylpyrrolidone (80 mL) were added 1-(oxbutacyclo-3-yl)piperazine (10750 mg, 75.7 mmol) and N,N-diisopropylethylamine (7813 mg, 60.5 mmol). The resulting mixture was heated overnight at 120° C. in sealed tube. After the reaction was completed, water (500 mL) was added. The mixture was extracted three times with ethyl acetate (100 mL). The combined organic phases were washed three times with water (80 mL) and once with saturated brine (80 mL), dried over anhydrous sodium sulfate and concentrated. 80 mL of solvent (petroleum ether:ethyl acetate=10:1) was added and pulped for 6 hours. The solid was filtered and dried to afford the title compound 4-2 (10200 mg, 79.60), as an off-white solid. MS (ESI): m/z=424.2[M+H]$^+$.

At 0° C., trifluoroacetic acid (30 mL) was added to the solution of Example 4-2 (8460 mg, 20 mmol) in dichloromethane (60 mL). The solution was stirred at 0° C. for 3 hours. After the reaction was completed, the solution was concentrated and then water (10 mL) was added. Ammonia was added dropwise to adjust to pH9. After purified on a reversed-phase column (mobile phase: acetonitrile/ammonium bicarbonate aqueous solution), the title compound (6000 mg, 92.8%) was afforded as a white solid. MS (ESI): m/z=324.0 [M+H]$^+$. $^1$HNMR (400 MHz, CD$_3$OD) δ 8.15 (s, 2H), 6.94 (s, 0.5H), 6.73 (s, 0.5H), 4.69 (t, J=6.7 Hz, 2H), 4.62 (t, J=6.2 Hz, 2H), 4.52 (dd, J=3.6, 0.8 Hz, 2H), 3.73 (t, J 3.9 Hz, 4H), 3.53-3.45 (i, 1H), 3.43 (d, J=2.4 Hz, 2H), 2.38 (t, J=3.9 Hz, 4H).

The following compounds were obtained using a method similar to those in Example 1 and 4 by replacing the corresponding starting materials.

| Number | Compound structure | LCMS, NMR |
|---|---|---|
| 5 | ![structure] | MS (ESI): m/z = 352.1[M + H]$^+$. $^1$HNMR (400 MHz, CD$_3$OD) δ 8.21 (s, 2H), 8.20 (d, J = 82.8 Hz, 1H), 4.71 (t, J = 6.8 Hz, 2H), 4.61 (d, J = 6.0 Hz, 2H), 4.58 – 4.57 (m, 2H), 3.73 (d, J = 6.8 Hz, 2H), 3.51 (d, J = 2.0 Hz, 2H), 3.47 – 3.41 (m, 1H), 2.44 (d, J = 6.8 Hz, 2H), 2.17 (s, 2H), 1.51 (s, 6H). |
| 6 | ![structure] | MS (ESI): m/z = 350.6 [M + H]$^+$. $^1$HNMR (400 MHz, CD$_3$OD) δ 8.15 (s, 2H), 6.87 (d, J = 83.2 Hz, 1H), 4.75 (t, J = 2.0 Hz, 2H), 4.58 (t, J = 2.0 Hz, 2H), 4.56 – 4.53 (m, 2H), 4.15 – 4.11 (m, 2H), 3.79 – 3.73 (m, 1H), 3.46 – 3.45 (m, 2H), 3.26 – 3.21 (m, 2H), 3.12 – 3.09 (m, 2H), 1.93 – 1.87 (m, 2H), 1.66 – 1.58 (m, 2H). |

-continued

| Number | Compound structure | LCMS, NMR |
|---|---|---|
| 7 | 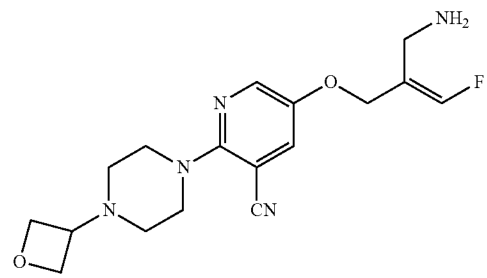 [SMILES: N#Cc1cc(OC/C(=C/F)CN)cnc1N1CCN(C2COC2)CC1] | MS (ESI): m/z = 348.6 [M + H]⁺.<br>¹HNMR (400 MHz, CD₃OD) δ 8.20 (d, J = 3.2 Hz, 1H), 7.70 (d, J = 2.8 Hz, 1H), 8.20 (d, J = 82.8 Hz, 1H), 4.72 (t, J = 6.8 Hz, 2H), 4.64 (d, J = 6.0 Hz, 2H), 4.59 – 4.52 (m, 2H), 3.60 – 3.57 (m, 1H), 3.53 – 3.50 (m, 6H), 2.52 (d, J = 4.2 Hz, 4H). |
| 8 | 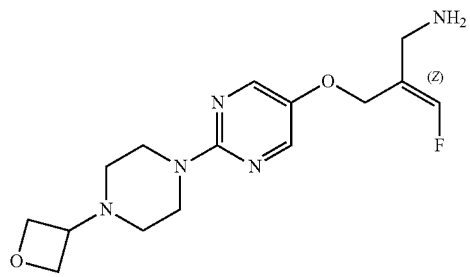 [SMILES: NC/C(=C/F)COc1cnc(N2CCN(C3COC3)CC2)nc1] | MS (ESI): m/z = 323.9 [M + H]⁺.<br>¹H NMR (400 MHz, CD₃OD) δ 8.50 – 8.39 (m, 1H), 8.15 (s, 2H), 7.01 (d, J = 81.2 Hz, 1H), 4.73 (d, J = 2.4 Hz, 2H), 4.65 (s, 2H), 4.58 (s, 2H), 3.74 – 3.66 (m, 4H), 3.59 (d, J = 2.4 Hz, 2H), 3.49 – 3.40 (m, 1H), 2.37 – 2.30 (m, 4H). |
| 9 | 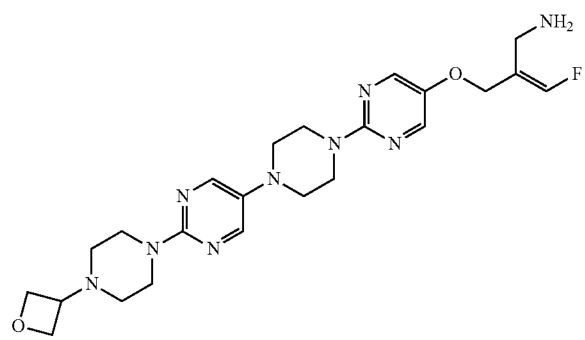 [SMILES: NC/C(=C\F)COc1cnc(N2CCN(c3cnc(N4CCN(C5COC5)CC4)nc3)CC2)nc1] | MS (ESI): m/z = 486.2 [M + H]⁺.<br>¹HNMR (400 MHz, CD₃OD) δ 8.24 (s, 2H), 8.18 (s, 2H), 7.13 (d, J = 80.5 Hz, 1H), 4.83 – 4.76 (m, 4H), 4.56 – 4.52 (m, 2H), 4.37 (td, J = 7.0, 3.6 Hz, 1H), 3.87 – 3.81 (m, 4H), 3.75 (s, 2H), 3.13 – 3.08 (m, 4H). |
| 10 | 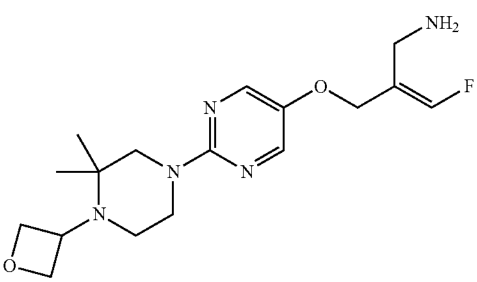 [SMILES: CC1(C)CN(c2ncc(OC/C(=C/F)CN)cn2)CCN1C1COC1] | MS (ESI): m/z = 352.6 [M + H]⁺.<br>¹HNMR (400 MHz, CD₃OD) δ 8.17 (s, 2H), 7.15 (d, J = 81.2 Hz, 1H), 4.82 – 4.78 (m, 2H), 4.65 – 4.62 (m, 2H), 4.58 – 4.56 (m, 2H), 4.46 – 4.38 (m, 1H), 3.86 – 3.83 (m, 2H), 3.79 (d, J = 2.0 Hz, 2H), 3.61 (s, 2H), 2.86 – 2.84 (m, 2H), 1.35 – 1.08 (m, 6H). |
| 11 | 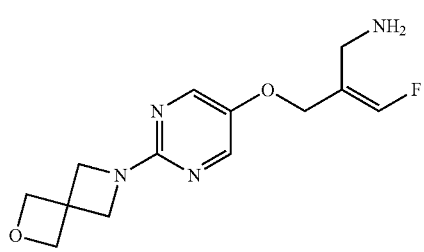 [SMILES: NC/C(=C\F)COc1cnc(N2CC3(COC3)C2)nc1] | MS (ESI): m/z = 280.9 [M + H]⁺<br>¹HNMR (400 MHz, CDCl₃) δ 8.10 (s, 2H), 6.68 (d, J = 81.9 Hz, 1H), 4.83 (s, 4H), 4.45 (s, 2H), 4.21 (d, J = 6.7 Hz, 4H), 3.57 (s, 2H). |

| Number | Compound structure | LCMS, NMR |
|---|---|---|
| 12 | (structure) | MS (ESI): m/z = 322.9. [M + H]⁺.<br>$^1$HNMR (400 MHz, CD$_3$OD) δ 8.43 (s, 2H), 7.26 (d, J = 80.6 Hz, 1H), 4.77 – 4.67 (m, 4H), 3.84 (s, 2H), 3.52 (s, 1H), 3.33 (s, 3H), 2.36 – 2.26 (m, 2H), 2.15 – 2.00 (m, 6H). |

Biological Test Example 1: Assay of In Vitro Inhibitory Activity of the Compounds on SSAO/VAP-1

This assay was used to evaluate the in vitro inhibitory activity of the compounds on SSAO/VAP-1 of different species. Recombinant human SSAO protein, mouse SSAO protein or rat SSAO protein (provided by Eli Lilly) were used. The enzyme activity detection kit, MAO-Glo Assay kit (V1402) was purchased from Promega. Enzyme reaction buffer (50 mM HEPES, 120 mM NaCl, 5 mM KCl, 2 mM CaCl$_2$, 1.4 mM MgCl$_2$, 0.001% Tween-20, pH7.4) was prepared. The test compound was dissolved in DMSO and diluted by 3-fold concentration in gradient. The final concentration of test compound in a 10 μL reaction system was 1 μM to 0.05 nM when SSAO was detected. The content of DMSO in the detection reaction was 1%. After the solution of test compound in DMSO was diluted in the enzyme reaction buffer at a volume ratio of 1:25, 2.5 μL of which was added to each well of detection plate, two replicates for each concentration. 5 μL of SSAO protein diluted in the enzyme reaction buffer was added to each well, the final concentration of which was 10 nM to 80 nM in 10 μL reaction system. The mixture was incubated at room temperature for 10 minutes. 2.5 μL of the reaction substrate diluted in the enzyme reaction buffer was added to each well, the final concentration of which was 10 μM in 10 μL reaction system. After the mixture was reacted at room temperature for 120 minutes, 10 μL of detection reagent was added to each well. The reaction solution was incubated for 20 minutes at room temperature, and the plate was read with Synergy Neo 2 for detection. The value was converted into inhibition rate by the following formula:

Inhibition rate=(Signal$_{positive}$−Signal$_{test}$)/(Signal$_{positive}$−Signal$_{negative}$)×100%

Signal$_{positive}$ was positive control without test compound. Signal$_{negative}$ was negative control without test compound and SSAO enzyme, and Signal$_{test}$ was detection value of each compound at different concentrations. IC$_{50}$ value was calculated by using 4 parameter curve fitting. For compounds with an inhibition rate of less than 50% within test range of the compound, IC$_{50}$ value was reported as greater than the highest tested concentration.

After testing, the compounds in the examples of the present invention can effectively inhibit the SSAO/VAP-1 enzyme activity of different species, and the results are shown in Table 1.

Biological Test Example 2: Assay of Inhibitory Activity of the Compounds on MAO-A and MAO-B Recombinant human MAO-A and MAO-B protein was purchased from Sigma (M7316, M7441). Other reagents are the same as Biological Test Example 1. The final concentration of test compound in 10 μL reaction system was 100 μM to 5 nM when MAO-A and MAO-B were detected. The final concentrations of MAO-A and MAO-B protein in 10 μL reaction system were 70 nM and 300 nM, respectively, while other reaction conditions were the same as those in Biological Test Example 1. Data analysis and IC$_{50}$ calculation method were the same as those in Biological Test Example 1. For compounds with an inhibition rate of less than 50% within test range of the compound, IC$_{50}$ value was reported as greater than the highest tested concentration. The results are shown in Table 1.

Biological Test Example 3: Assay of Inhibitory Activity of the Compounds on AOC1

Recombinant human AOC1/DAO protein was purchased from R&D systems (Cat: 8298-AO). Amplex UltraRed was purchased from Thermo scientific (Cat: A36006). HRP (Cat: P8250) and Putrescine (Cat: V900377) were purchased from Sigma. Enzyme reaction buffer (50 mM HEPES, 120 mM NaCl, 5 mM KCl, 2 mM CaCl$_2$, 1.4 mM MgCl$_2$, 0.001% Tween-20, pH7.4) was prepared. Test compound was dissolved in DMSO and diluted by 3-fold concentration in gradient. The final concentration of test compound in 10 μL reaction system was 100 μM to 5 nM when AOC1 was detected. The content of DMSO in detection reaction was 1%. After the solution of test compound in DMSO was diluted in the enzyme reaction buffer at a volume ratio of 1:25, 10 μL of mixture was added to each well of detection plate. 4× substrate mixture (containing 400 μM Putrescine, 4 U/mL HRP, 4 μM Amplex UltraRed) was prepared in the enzyme reaction buffer, 10 μL of which was added to each well. 20 μL of AOC1 protein diluted in enzyme reaction buffer was added to each well at final concentration 0.4 nM in 40 μL reaction system. Synergy Neo 2 was used to read the plate for detection. The instrument was set at 30° C., 530 nM excitation wavelength, 590 nm emission wavelength. Detection was conducted once every minute for 30 minutes continuously. The enzyme activity was calculated based on the increased signal of each well from the 10th minute to the 30$^{th}$ minute. The value was converted into inhibition rate by the following formula Inhibition rate=(Signal$_{positive}$−Signal$_{test}$)/(Signal$_{positive}$−Signal$_{negative}$)×100%

Signal$_{positive}$ was positive control without test compound. Signal$_{negative}$ was negative control without test compound and AOC1, and Signal$_{test}$ was detection value of different compounds at each concentration. IC$_{50}$ value was calculated by using 4 parameter curve fitting. For compounds with an inhibition rate of less than 50% within test range of the compound, $IC_{50}$ value was reported as greater than the highest tested concentration.

The results were shown in Table 1.

Biological Test Example 4: Assay of Inhibitory Activity of the Compounds on AOC2

Recombinant human AOC2 protein (provided by Eli Lilly). Other reagents are the same as those in Biological Test Example 1. The final concentration of test compound in 10 μL reaction system was 100 μM to 5 nM when AOC2 was detected, while other reaction conditions were the same as those in Biological Test Example 1. Data analysis and $IC_{50}$ calculation method were the same as those in Biological Test Example 1. For compounds with an inhibition rate of less than 50% within test range of the compound, $IC_{50}$ value was reported as greater than the highest tested concentration.

The results were shown in Table 1.

intestine, lung, liver, and kidney were respectively collected 24 hours after administration (the animals were perfused with PBS before the collection of small intestine, lung, liver, and kidney) and stored in a −80° C. refrigerator until analysis. Each tissue was homogenized in tissue homogenate lysis buffer (20 mM HEPES, pH 7.4, 150 mM NaCl, 1 mM EDTA, 1 mM EGTA, 1% Triton X-100 and 1× Roche Complete protease inhibitor tablet). The homogenate was centrifuged at 12000 rpm at 4° C. for 30 minutes to remove tissue fragments. 5 μL of supernatant and 2 μL of mixture of Clogyline (10 μM) and Pargyline (10 μM) were incubated for 10 minutes at room temperature. Then 2 μL of substrate from MAO-Glo assay kit was added to the mixture, and reacted at room temperature for 60 minutes. Detection reagents were added to quench the reaction according to instructions. The fluorescein data was read by Biotek Neo2. The activity of monoamine oxidase in tissues that is not sensitive to MAO inhibitors was used to represent the activity of SSAO. Percentage of SSAO activity in admin-

TABLE 1

In vitro inhibitory activity $IC_{50}$ (nM) of the compounds against SSAO of different species and other amine oxidases

| Example | Human SSAO | AOC1 | AOC2 | MAO-A | MAO-B | Rat SSAO | Mouse SSAO |
|---------|------------|------|------|-------|-------|----------|------------|
| 1  | A | E  | F  | I | K | NA | NA |
| 2  | A | D  | G  | H | K | L  | L  |
| 3  | A | D  | G  | H | K | NA | NA |
| 4  | A | E  | G  | I | K | L  | L  |
| 5  | B | E  | F  | I | K | NA | NA |
| 6  | B | E  | F  | I | K | NA | NA |
| 7  | C | E  | G  | I | J | NA | NA |
| 8  | A | E  | G  | H | J | NA | NA |
| 9  | A | D  | F  | I | K | NA | NA |
| 10 | B | E  | G  | I | K | NA | NA |
| 11 | C | NA | NA | H | K | NA | NA |
| 12 | A | E  | G  | H | K | L  | L  |

| Enzyme | Letter | Inhibitory activity $IC_{50}$ (nM) |
|--------|--------|-------------------------------------|
| Human SSAO | A | <10 |
|  | B | 10~50 |
|  | C | >50 |
| AOC1 | D | 100~10000 |
|  | E | >10000 |
| AOC2 | F | 100~1000 |
|  | G | >1000 |
| MAO-A | H | 2000~100000 |
|  | I | >100000 |
| MOA-B | J | 5000~20000 |
|  | K | >20000 |
| Rat SSAO | L | <100 |
| Mouse SSAO | L | <100 |

The above results show that the compounds of the present invention exhibit excellent inhibitory activity against AOC3, and quite good selectivity for amine oxidase subtypes.

Biological Test Example 5: Assay of Inhibitory Activity of Compounds on SSAO/VAP-1 in Mouse/Rat Model MAO-Glo Assay kit (Promega, V1402) was used to determine the activity of SSAO in animal tissues. After test compounds were adminstered to the animal, SSAO enzyme activity was calculated by measuring the activity of the monoamine oxidases in the animal tissue homogenate that was insensitive to MAO inhibitors Clogyline and Pargyline. The compounds were orally administered to rats at different doses, and same volume of vehicle was orally administered to control animals. Animal plasma, brain, retina, small istered animals was compared with that of control animals to calculate the compound inhibition rate.

The test results show that the compounds can effectively inhibit the activity of SSAO in different tissues of animals after administration. The results were shown in Table 2 and Table 3.

TABLE 2

The remaining SSAO activity percentage (SSAO activity %) at 24 hours post a single administration of compound

| Example | Dose (mg/kg) | Plasma | Brain | Retina |
|---------|--------------|--------|-------|--------|
| 2 | 0.6 | 24.3 ± 5.2 | 49.1 ± 21.2 | 28.7 ± 8.5 |
| 3 | 1   | 15.2 ± 2.6 | 55.6 ± 10.5 | 8.9 ± 3.2  |

TABLE 2-continued

The remaining SSAO activity percentage (SSAO activity %) at 24 hours post a single administration of compound

| Example | Dose (mg/kg) | Plasma | Brain | Retina |
|---|---|---|---|---|
| 10 | 0.6 | 5.8 ± 2.1 | 27.3 ± 1.8 | 8 ± 0.8 |
| 12 | 1 | 25.6 ± 3 | 63.1 ± 12.1 | 24.6 ± 3.5 |

The data in the table are shown as mean ± SEM, N = 3.

TABLE 3

The remaining SSAO activity percentage (SSAO activity %) of the compound of Example 4 at 24 hours post a single administration

| Dose (mg/kg) | Plasma | Brain | Retina | Liver | Lung | kidney | Small intestine |
|---|---|---|---|---|---|---|---|
| 15 | 1.1 ± 0.4 | 4 ± 1.7 | 3 ± 2.2 | −2.4 ± 5.4 | 2.2 ± 0.2 | 2.4 ± 1.3 | 1.1 ± 0.9 |
| 3 | 1.8 ± 0.2 | 22.1 ± 7.7 | 5.2 ± 2.4 | 5.3 ± 3.2 | 4.6 ± 2.5 | 0.7 ± 1.8 | 11.1 ± 4.4 |
| 0.6 | 12.9 ± 2.2 | 26.5 ± 11.8 | 8 ± 1.2 | 3 ± 7.6 | 14.1 ± 3.8 | 26.2 ± 10.1 | 38.9 ± 3.2 |
| 0.12 | 33.7 ± 1.9 | 75.4 ± 7.4 | 25.1 ± 5.3 | 40.1 ± 8.2 | 39.8 ± 11.3 | 46.3 ± 3.5 | 96.9 ± 21.7 |
| 0.025 | 58.6 ± 4.2 | 143.1 ± 68.3 | 49.1 ± 7.1 | 14.4 ± 8.1 | 64 ± 20.3 | 58.7 ± 12.1 | — |
| 0.005 | 61.7 ± 8.2 | 98.3 ± 25.4 | 65 ± 14 | 107.7 ± 33.5 | 94.9 ± 17.2 | 99.2 ± 4.1 | — |
| Control | 99.89 ± 8.8 | 100 ± 18.7 | 100 ± 23 | 99.89 ± 14.4 | 100 ± 36 | 99.89 ± 5.7 | 100 ± 3.2 |

The data in the table are shown as mean ± SEM, N = 3.

The data in the table are shown as mean±SEM, N=3.

Biological Test Example 6: Pharmacodynamics Study of SSAO Compound in Ocular Inflammation-Related Disease Model 22 rats (7-8 weeks, 220-250 g) were divided into 3 groups, which were control group (6), model group (8) and compound treated group (8). For the model group and compound treated group, ocular inflammation was induced by a single injection of 8 µg/100 µL lipopolysaccharide (Sigma-Aldrich-L2880) into the footpad. The rats were grouped according to their body weight 1 h before induction. Example 4 compound (6 mg/kg, 10 mL/kg) or vehicle (10 mL/kg) were orally administered respectively. 24 hours after induction, the anterior aqueous humor was collected and the eyeballs were removed to dissect the retina. Ocular inflammation was quantitatively evaluated by measuring the protein concentration and cell number in the aqueous humor. qPCR method was used to verify changes in the expression of ocular retinal inflammation-related genes.

Methods for Determining the Cell Number and Protein Concentration in Aqueous Humor:

10 µL of aqueous humor was diluted in 40 µL of PBS and mixed, then 25 µL of mixture was mixed with 75 µL of PBS, and centrifuged at 300 g for 5 min at 4° C. 55 µL of supernatant was aspirated carefully and the protein concentration was determined according to the method described in the BCA Protein Assay Kit (Pierce-23227); after the remaining sample was resuspended, 40 µL of cell suspension was added into 100 µL of 1% FBS/PBS to analyze and count live cells using NovoCyte 3130 flow cytometry after excluding cell debris.

Compared with control group, total protein concentration of the model group in the aqueous humor increased significantly (mean±SEM: 9730.04±1232.30 µg/mL VS 3147.42±404.79 µg/mL), and cell number increased significantly (mean±SEM: 48.28±21.46*10^4 cell/mL VS 2.69±0.45*10^4 cell/mL), suggesting that ocular inflammatory disease model was successfully induced.

Compared with model group, protein concentration was reduced (mean±SEM: 7275.44±622.66 VS 9730.04±1232.30 µg/mL), and cell number was reduced significantly in compound treated group (mean±SEM: 5.07±0.80*10^4 cell/mL VS 48.28±21.46*10^4 cell/mL), suggesting that Example 4 compound can significantly alleviate ocular inflammation-related disease symptoms. As shown in FIG. 1, Example 4 compound can significantly alleviate ocular inflammation-related symptoms in LPS-induced inflammatory disease model in rats. FIG. 1A. Changes in the concentration of protein in aqueous humor (µg/mL); FIG. 1B. Changes in cell number in aqueous humor (*10^4/mL).

Determination of Expression Level of Inflammation-Related Genes in Retina:

1) Primers were synthesized, with the information shown as follows:

| Primer name | sequence (5' to 3') | SEQ ID NO. |
|---|---|---|
| Rat-Alox5ap-F | CCTTCGCTGGGCTGATGTAT | 1 |
| Rat-Alox5ap-R | ATAGGATGATCCGCTTGCCG | 2 |
| Rat-Socs3-F | CCCCGCTTTGACTGTGTACT | 3 |
| Rat-Socs3-R | AAAGGAAGGTTCCGTCGGTG | 4 |
| Rat-UBC-F | ACACCAAGAAGGTCAAACAGG | 5 |
| Rat-UBC-R | AGACACCTCCCCATCAAACC | 6 |
| Rat-TLR7-F | AGCTCTGTTCTCCTCCACCA | 7 |
| Rat-TLR7-R | ACCATCGAAACCCAAGGACTC | 8 |

2) Retinal RNA was extracted according to operating instructions of RNA extraction kit (RNeasy Mini Kit, Qiagen-74104), and then the RNA was reverse-transcribed into cDNA (High Capacity cDNA Reverse Transcription Kits, ABI-4374966). The obtained cDNA was diluted 10 times to serve as qPCR reaction template. According to instructions of Power SYBR Green kit (ABI-A25918), qPCR reaction was performed on CFX384 Real-Time qPCR equipment. Quantitative analysis of expression changes for each gene expression was performed using CFX Maestro software by ΔΔCt method, with UBC as internal housekeeping gene.

Figure 2:
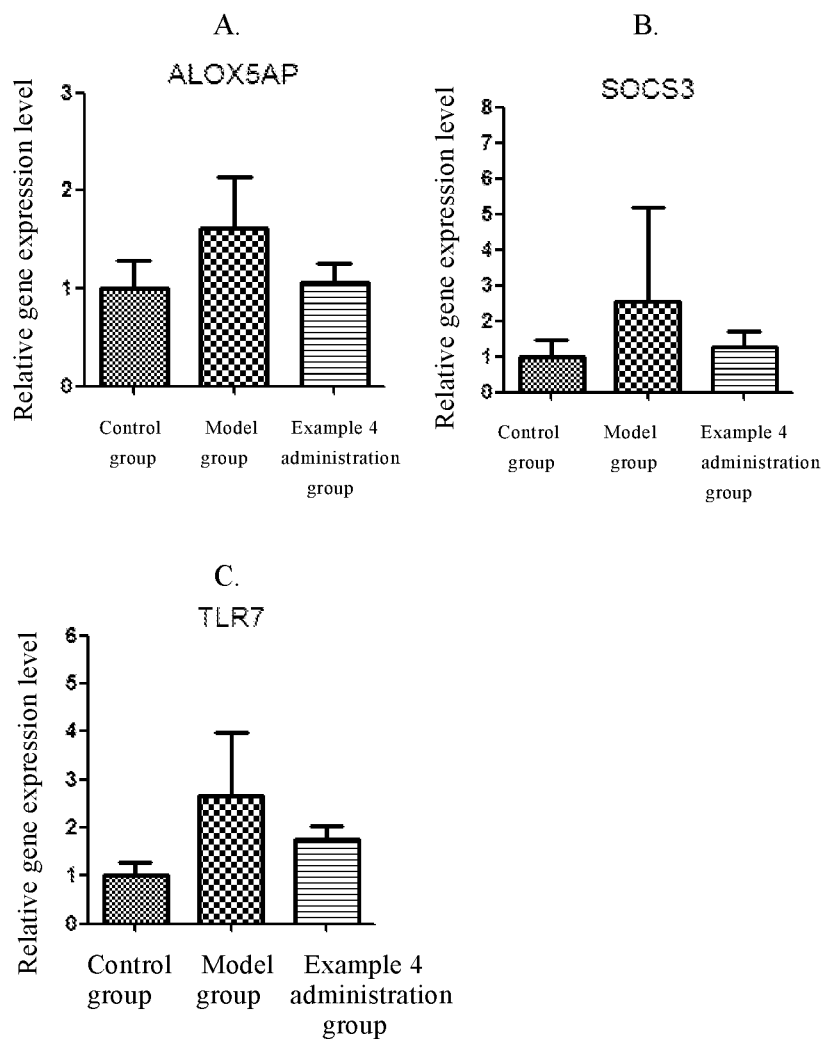
FIG. 2 shows the effect of the compound herein on the expression of inflammatory signal pathway genes in retina in LPS-induced rat inflammatory disease model.

Compared with control group, gene expression level of ALOX5AP, SOCS3 and TLR7 increased significantly in model group. Compared with model group, gene expression levels of ALOX5AP, SOCS3 and TLR7 decreased significantly in compound treated group, as shown in FIG. 2. After analysis, all of ALOX5AP, SOCS3 and TLR7 gene expression were regulated by NFkB signaling pathway, which was a very important molecular signaling pathway in inflammatory diseases.

FIG. 2: Example 4 compound can significantly reduce expression level of inflammation-related genes in retina in LPS-induced inflammatory disease model of rats. A. ALOX5AP; B. SOCS3; C. TLR7.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound according to Formula I, or stereoisomers or racemates thereof, or pharmaceutically acceptable salts thereof:

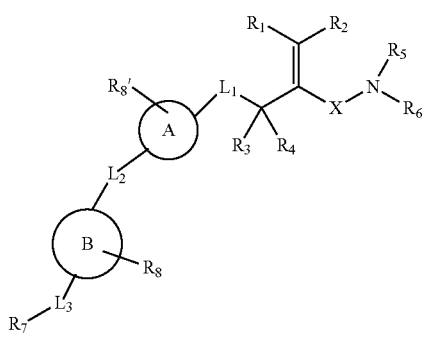

I wherein,
A is none;
B is substituted or unsubstituted 6 membered heteroaromatic ring; wherein the heteroaromatic ring contains 1-2 nitrogen atoms;
$L_1$ is —O—;
$L_2$ is none;
$L_3$ is a substituted or unsubstituted 5-12 membered heterocyclic ring, the heterocyclic ring contains 1-3 heteroatoms selected from nitrogen, oxygen or sulfur;
$R_1$ is F, and $R_2$ is H; or $R_1$ is H, and $R_2$ is F;
$R_3$ and $R_4$ are H;
$R_5$ and $R_6$ are each independently a hydrogen;
$R_7$ is a 4-6 membered heterocyclic ring containing 1 oxygen atom;
$R_8$ is selected from the group consisting of H, and —CN;
$R_8'$ is none;
X is —$CR_{11}R_{12}$; and
$R_{11}$ and $R_{12}$ are each independently H;
with the proviso that the above groups constitute a chemically stable structure;
wherein unless otherwise specified, the above-mentioned "substituted" means one or more hydrogen atoms on the group being substituted by $C_1$-$C_6$ alkyl.

2. The compound of claim 1, or stereoisomers or racemates thereof, or pharmaceutically acceptable salts thereof, wherein $L_3$ is a structure selected from the group consisting of piperazine ring

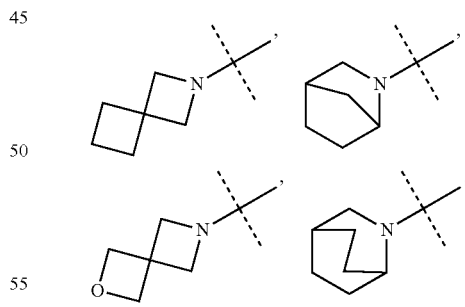

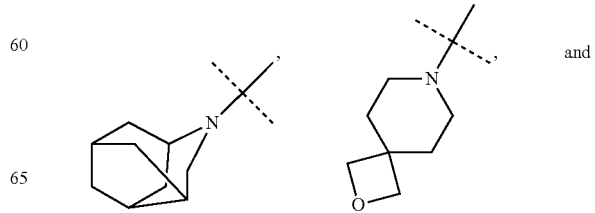

and

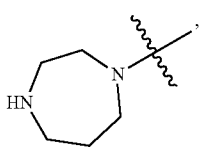

wherein L₃ can be substituted or unsubstituted.

3. The compound of claim 1, or stereoisomers or racemates thereof, or pharmaceutically acceptable salts thereof, wherein the compound has a structure shown in the following formula II:

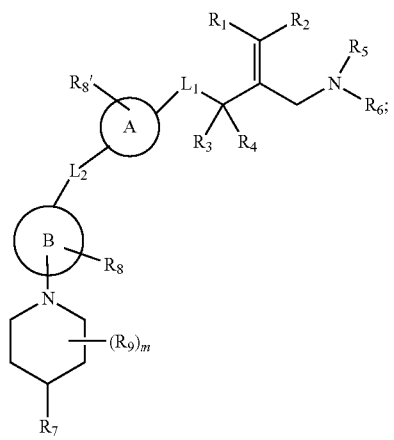

and wherein, $R_9$ is $C_1$-$C_6$ alkyl, m is 0, 1, 2, 3, or 4.

4. The compound of claim 1, or stereoisomers or racemates thereof, or pharmaceutically acceptable salts thereof, wherein $R_7$ is 4-membered heterocyclic ring containing 1 oxygen atom.

5. The compound of claim 1, or stereoisomers or racemates thereof, or pharmaceutically acceptable salts thereof, wherein $R_7$ is

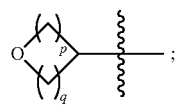

wherein, the p and q are each independently selected from the group consisting of 0, 1, 2, 3 and 4, and the sum of p and q is ≥1.

6. The compound of claim 1, wherein the compound is selected from the following group:

| Compound number | Compound structure |
|---|---|
| 10 | 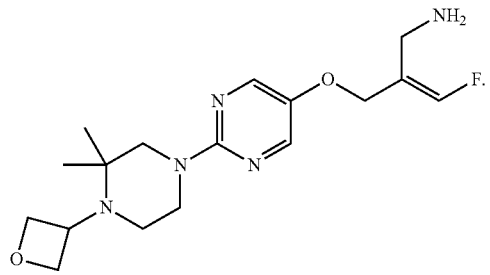 [SMILES: CC1(C)CN(c2ncc(OC/C(=C/F)CN)cn2)CCN1C1COC1] |

7. A pharmaceutical composition, comprising therapeutically effective amount of the compound according to claim 1, or stereoisomers or racemates thereof, or pharmaceutically acceptable salts thereof, and a pharmaceutically acceptable excipient.

8. A method for inhibiting semicarbazide-sensitive amine oxidase (SSAO), the method comprising administering an effective amount . . . a pharmaceutically acceptable salt thereof, or administering a pharmaceutical composition comprising the compound of Formula I, the stereoisomer or racemate thereof, or the pharmaceutically acceptable salt thereof and a pharmaceutically acceptable excipient to a subject in need thereof.

9. The method of claim 8, wherein the subject is a human patient having an ocular disease.

10. The method of claim 9, wherein the ocular disease is uveitis or macular degeneration.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ccttcgctgg gctgatgtat                                                  20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ataggatgat ccgcttgccg                                                  20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ccccgctttg actgtgtact                                                  20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
aaaggaaggt tccgtcggtg                                                  20

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
acaccaagaa ggtcaaacag g                                                21

<210> SEQ ID NO 6
<211> LENGTH: 20
<212> TYPE: DNA
<213> ORGANISM: Artificial Sequence
```

```
<220> FEATURE:
<223> OTHER INFORMATION: primer

<400> SEQUENCE: 6
agacacctcc ccatcaaacc                                          20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
agctctgttc tcctccacca                                          20

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
accatcgaaa cccaaggact c                                        21
```